United States Patent
Kuwae et al.

(10) Patent No.: US 10,993,740 B2
(45) Date of Patent: May 4, 2021

(54) SURGERY SYSTEM AND ENDOSCOPE

(71) Applicant: FUJIFILM Corporation, Tokyo (JP)

(72) Inventors: Toshiharu Kuwae, Kanagawa (JP); Takumi Dejima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 344 days.

(21) Appl. No.: 16/012,777

(22) Filed: Jun. 20, 2018

(65) Prior Publication Data
US 2018/0296242 A1 Oct. 18, 2018

Related U.S. Application Data

(63) Continuation of application No. PCT/JP2016/089151, filed on Dec. 28, 2016.
(Continued)

(51) Int. Cl.
*A61B 1/00* (2006.01)
*A61B 17/34* (2006.01)
(Continued)

(52) U.S. Cl.
CPC ...... *A61B 17/3421* (2013.01); *A61B 1/00071* (2013.01); *A61B 1/00154* (2013.01);
(Continued)

(58) Field of Classification Search
None
See application file for complete search history.

(56) References Cited

U.S. PATENT DOCUMENTS

| | | | |
|---|---|---|---|
| 4,060,086 A | 11/1977 | Storz | |
| 4,753,222 A | * 6/1988 | Morishita | ............ A61B 1/0055 600/140 |

(Continued)

FOREIGN PATENT DOCUMENTS

| | | |
|---|---|---|
| EP | 1334690 | 8/2003 |
| JP | 2002125914 | 5/2002 |

(Continued)

OTHER PUBLICATIONS

"International Search Report (Form PCT/ISA/210) of PCT/JP2016/089151", dated Mar. 21, 2017, with English translation thereof, pp. 1-5.
(Continued)

*Primary Examiner* — Timothy J Neal
(74) *Attorney, Agent, or Firm* — JCIPRNET

(57) ABSTRACT

Provided are a surgery system that can ensure insulation between an endoscope and a treatment tool. The endoscope has an insertion part that is insertable into an overtube and has a distal end, a proximal end, and a longitudinal axis, and is locked to the movable body by an endoscope holding part. The endoscope has a first insertion part that is provided on a distal end side of the insertion part, a second insertion part that is provided on a proximal end side of the first insertion part and has an external diameter larger than that of the first insertion part, and a held part that is provided from a distal end of the second insertion part toward a proximal end side thereof, is held by the endoscope holding part, and has at least a surface formed of an insulating member having an insulation property.

10 Claims, 25 Drawing Sheets

Related U.S. Application Data

(60) Provisional application No. 62/275,793, filed on Jan. 7, 2016.

(51) Int. Cl.
  *A61B 1/313* (2006.01)
  *A61B 17/00* (2006.01)

(52) U.S. Cl.
  CPC ...... *A61B 1/3132* (2013.01); *A61B 17/00234* (2013.01); *A61B 17/3462* (2013.01); *A61B 2017/00862* (2013.01); *A61B 2017/347* (2013.01); *A61B 2017/3433* (2013.01); *A61B 2017/3445* (2013.01); *A61B 2017/3447* (2013.01)

(56) References Cited

U.S. PATENT DOCUMENTS

| | | | | |
|---|---|---|---|---|
| 4,899,787 | A * | 2/1990 | Ouchi | A61B 1/0055 138/131 |
| 4,944,287 | A * | 7/1990 | Takahashi | B21C 37/154 420/401 |
| 2015/0080650 | A1 | 3/2015 | Dejima et al. | |
| 2016/0022122 | A1 | 1/2016 | Dejima | |
| 2017/0007102 | A1 | 1/2017 | Dejima | |
| 2017/0007105 | A1 | 1/2017 | Dejima et al. | |
| 2018/0008309 | A1 | 1/2018 | Kuwae et al. | |

FOREIGN PATENT DOCUMENTS

| | | |
|---|---|---|
| WO | 2013176167 | 11/2013 |
| WO | 2014157476 | 10/2014 |
| WO | 2015147153 | 10/2015 |
| WO | 2015147155 | 10/2015 |
| WO | 2016152626 | 9/2016 |

OTHER PUBLICATIONS

"Written Opinion of the International Searching Authority of PCT/JP2016/089151" with English translation thereof, dated Mar. 21, 2017, p. 1-p. 7.

"Office Action of Japan Counterpart Application," with machine English translation thereof, dated Jul. 8, 2019, p. 1-p. 7.

"Office Action of Japan Counterpart Application," dated Apr. 25, 2019, with English translation thereof, p. 1-p. 6.

"Search Report of Europe Counterpart Application", dated Nov. 22, 2018, p. 1-p. 6.

"Office Action of Europe Counterpart Application", dated Aug. 18, 2020, p. 1-p. 3.

* cited by examiner

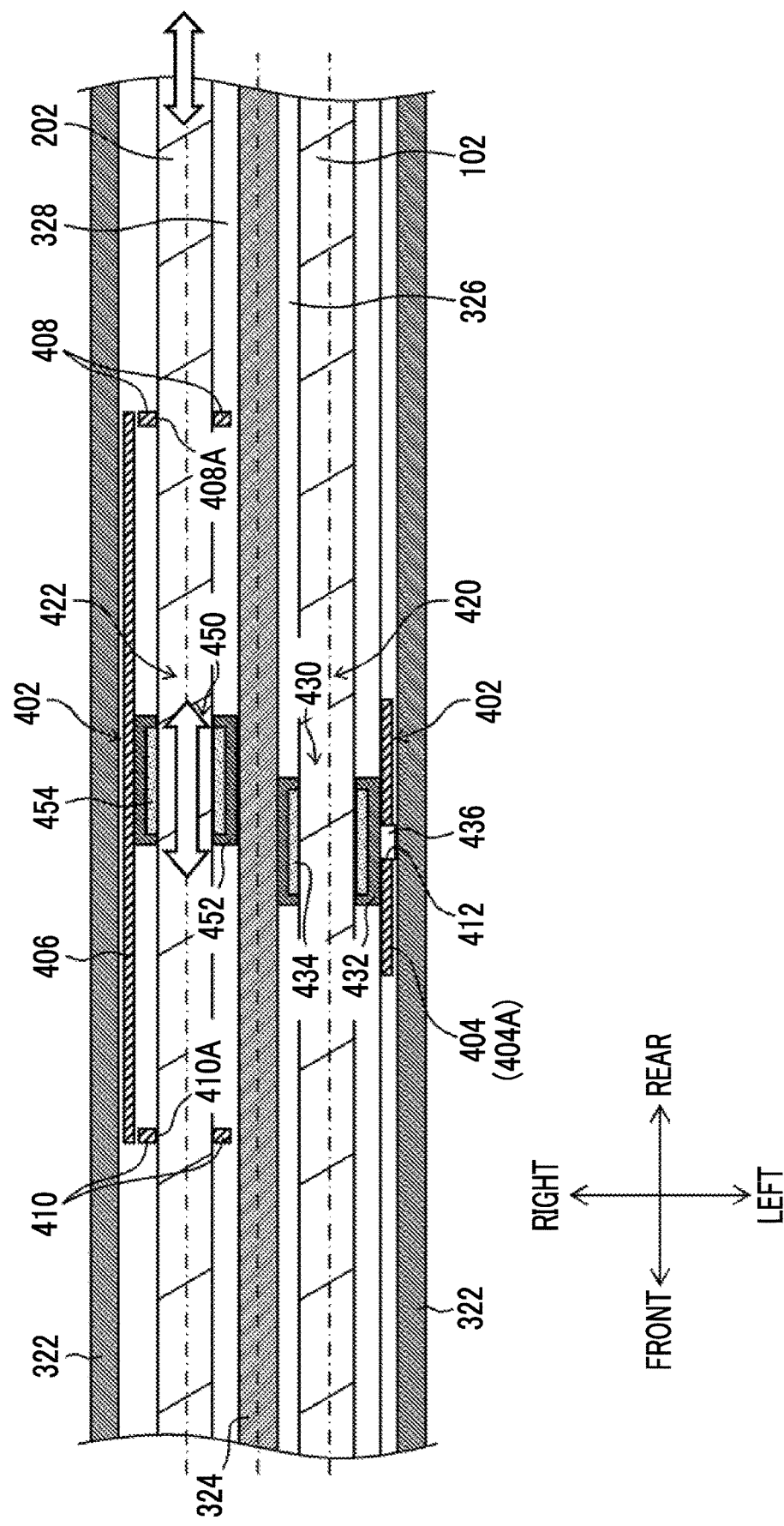

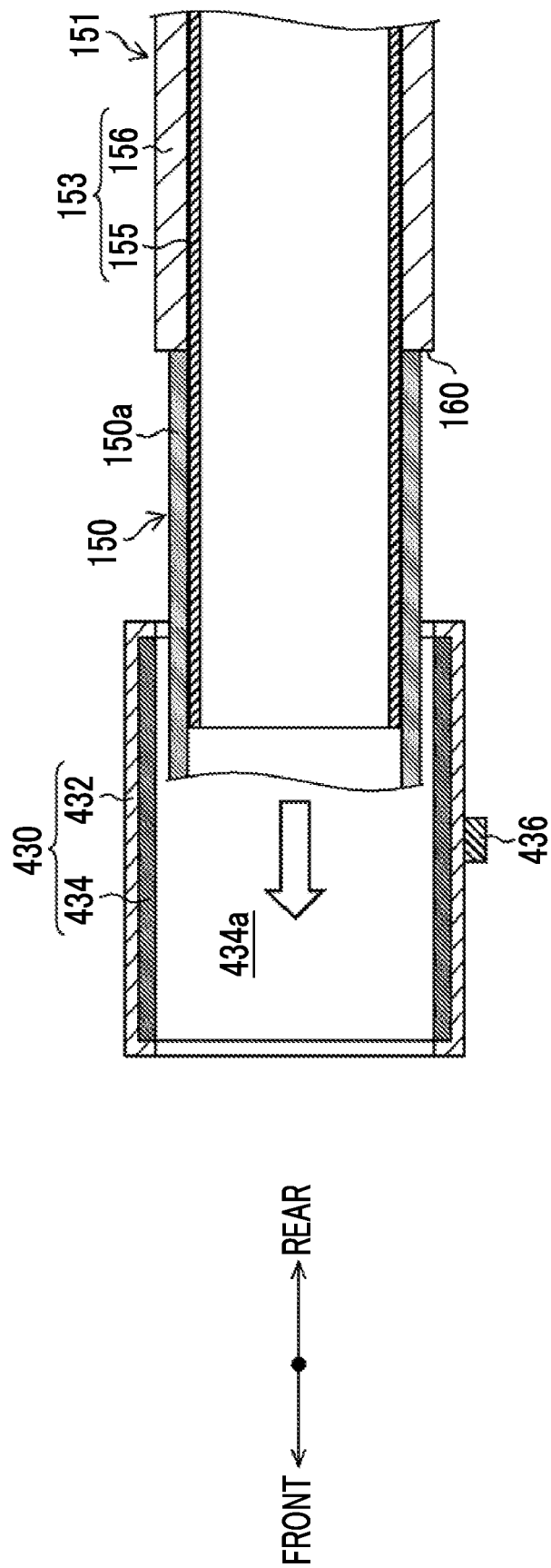

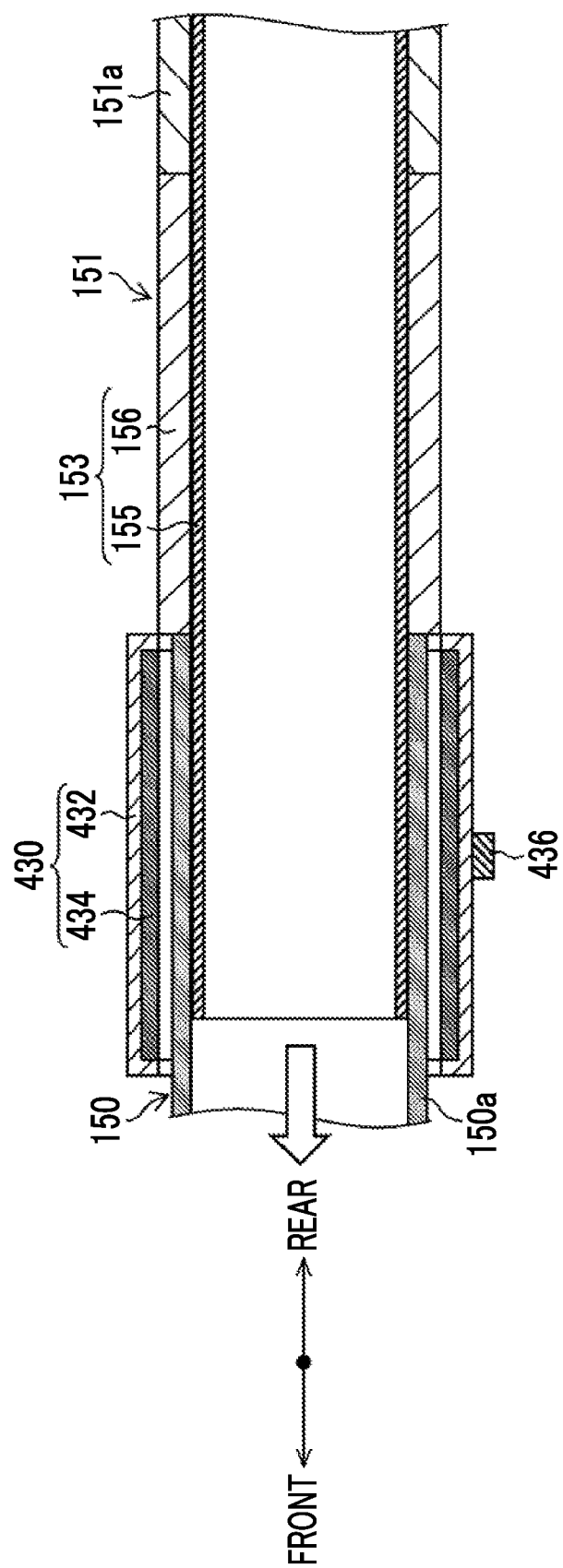

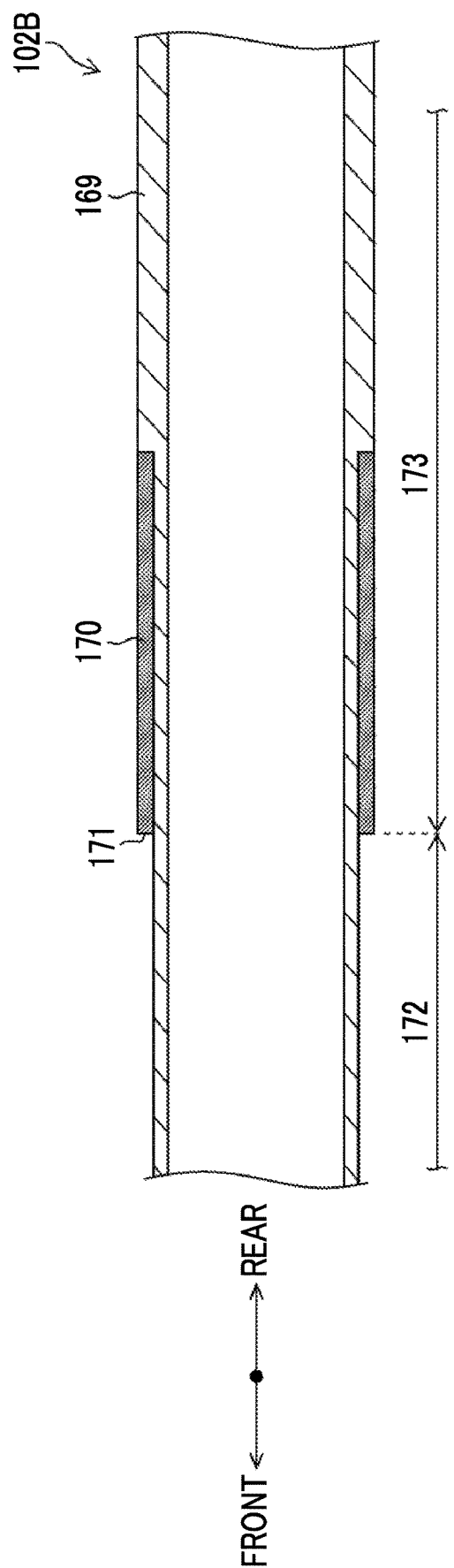

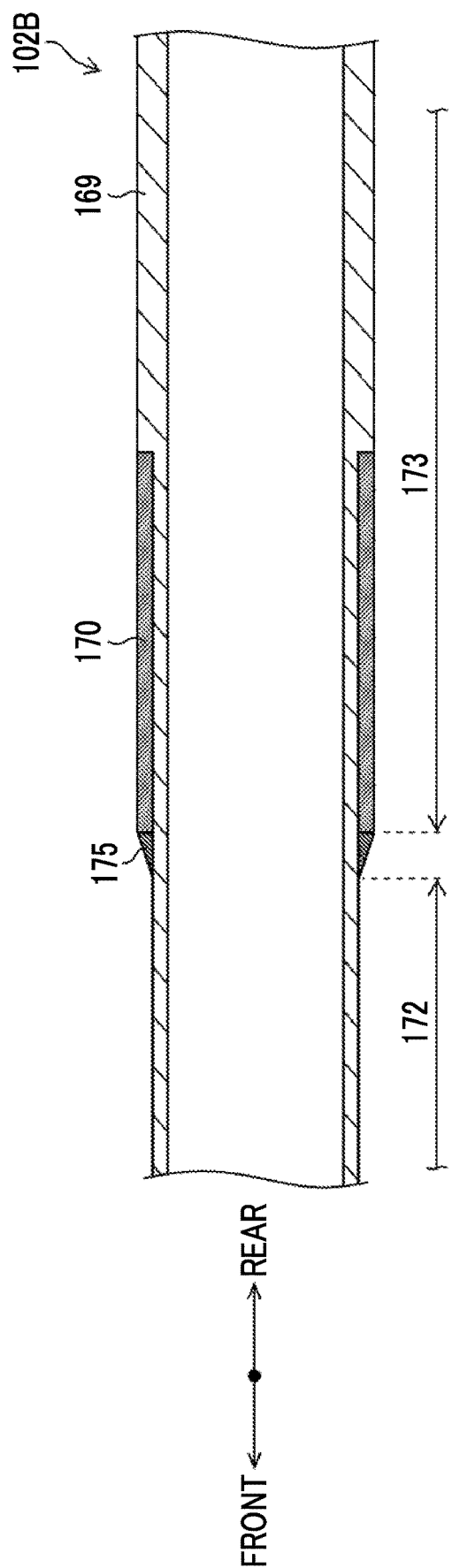

SURGERY SYSTEM AND ENDOSCOPE

CROSS-REFERENCE TO RELATED APPLICATIONS

The present application is a Continuation of PCT International Application No. PCT/JP2016/089151 filed on Dec. 28, 2016 claiming priority under 35 U.S.C § 119(a) to U.S. Provisional Application No. 62/275,793 filed on Jan. 7, 2016. Each of the above applications is hereby expressly incorporated by reference, in their entirety, into the present application.

BACKGROUND OF THE INVENTION

1. Field of the Invention

The present invention relates to a surgery system that holds an endoscope and a treatment tool with an overtube so as to be movable forward and backward, and an endoscope used in this surgery system.

2. Description of the Related Art

In recent years, since the invasion to a patient is small compared to surgery in which a laparotomy, a thoracotomy, or the like is performed, endoscopic surgery using endoscopes (rigid endoscopes), such as a laparoscope, has been widely performed. In the endoscopic surgery, a plurality of holes are made in a patient's body wall, an endoscope is inserted into a body cavity from one hole among the plurality of holes, and a treatment tool is inserted into the body cavity from another hole. Then, treatment of living body tissue is performed with the treatment tool while displaying endoscopic images obtained by the endoscope on a monitor to observe the living body tissue within the body cavity.

In such endoscopic surgery, an insertion part of the endoscope and an insertion part of the treatment tool can be inserted into the body cavity by using an overtube (also referred to as a trocar) having a plurality of insertion passages through which the insertion part of the endoscope and the insertion part of the treatment tool are inserted, respectively (refer to WO2013/176167A). By using the overtube described this WO2013/176167A, the number of holes to be made in the patient's body wall can be reduced, and the invasion to the patient can be suppressed.

Additionally, a movable body (the slider), which is movable in a longitudinal axis direction, is provided within the overtube described in WO2013/176167A. This movable body holds the endoscope and the treatment tool that are inserted along the insertion passages within the overtube, respectively, and moves the endoscope and the treatment tool forward and backward in the longitudinal axis direction in an interlocking manner. Accordingly, for example, in a case where the treatment tool is moved in the longitudinal axis direction, the endoscope can be moved in the longitudinal axis direction in an interlocking manner with this. For this reason, the visual field of the endoscope can be made to follow a portion to be treated, and an operator can always be provided with an endoscopic image optimal for treatment.

SUMMARY OF THE INVENTION

In recent years, since it is required to make the overtube thinner in order to suppress invasion to a patient, it is also necessary to thin the movable body. Here, in a case where the movable body is thinned, stiffness and dimensional accuracy decrease. In a case where deformation or poor accuracy resulting from shortage of stiffness is generated in the movable body, a sliding load during interlocking operation between the endoscope and the treatment tool increases. Therefore, there is a concern that the interlocking operation may not be possible depending on the case. Therefore, in order to maintain the stiffness and the dimensional accuracy while thinning the movable body, it is possible to form this movable body using metal. However, in a case where the movable body is formed of metal, the insulation between the endoscope and the treatment tool cannot be secured, and in a case where an electric current is applied to the treatment tool, there is a concern that leakage may occur on the endoscope side, and electronic components (a solid-state image pick-up element and the like) of an observation part of the endoscope may be damaged.

The invention has been made in view of such circumstances, and an object thereof is to provide a surgery system that can ensure insulation between an endoscope and a treatment tool even in a case where a movable body is formed of metal, and an endoscope used for this surgery system.

A surgery system for achieving the object of the invention comprises an overtube that has a distal end, a proximal end, and a longitudinal axis and holds a treatment tool and an endoscope so as to be movable forward and backward in a direction of the longitudinal axis. The overtube has a metallic movable body that is provided within the overtube and is movable in the longitudinal axis direction inside the overtube, an endoscope holding part that is provided at the movable body and holds the endoscope, and a treatment tool holding part that is provided at the movable body and holds the treatment tool. The surgery system further comprises an endoscope that has an insertion part which is insertable into the overtube and has a distal end, a proximal end, and a longitudinal axis and that is locked to the movable body by the endoscope holding part. The endoscope has a first insertion part that is provided on a distal end side of the insertion part, a second insertion part that is provided on a proximal end side of the first insertion part and has an external diameter larger than that of the first insertion part, and a held part that is provided from a distal end of the second insertion part toward a proximal end side thereof, is held by the endoscope holding part, and has at least a surface formed of an insulating member having an insulation property. The surgery system further comprises the treatment tool that is inserted into the overtube and locked to the movable body by the treatment tool holding part.

According to this surgery system, the insulation between the endoscope and the treatment tool can be ensured, and the held part of the insertion part can be simply held by the endoscope holding part in a case where an operator inserts the insertion part of the endoscope into the overtube.

In the surgery system related to another aspect of the invention, the endoscope holding part has a metallic holding frame, and an annular elastic holder that is provided within the holding frame and elastically hold the held part. By elastically holding the held part with the elastic holder, it is possible to adjust the rotation and the holding position of the insertion part.

In the surgery system related to still another aspect of the invention, the second insertion part is provided so as to be continuous with the first insertion part. Accordingly, the external diameter of the second insertion part can be simply made larger than the external diameter of the first insertion part.

In the surgery system related to a still another further aspect of the invention, a tapered part of which an external diameter becomes gradually larger from the first insertion part toward the second insertion part is provided between the first insertion part, and the second insertion part. Accordingly, the held part can be guided to the endoscope holding part and can be reliably held.

In the surgery system related to a still further aspect of the invention, the held part includes a tubular member having an insulation property. Accordingly, the insulation between the endoscope and the treatment tool is ensured.

In the surgery system related to a still further aspect of the invention, the endoscope has a third insertion part that is provided on the proximal end side of the second insertion part and has an external diameter smaller than that of the second insertion part. Accordingly, the sliding resistance in a case where the insertion part is rotated or moved forward and backward can be reduced.

In the surgery system related to a still further aspect of the invention, the endoscope has a fourth insertion part that is provided on the proximal end side of the second insertion part and has an external diameter larger than that of the second insertion part. Accordingly, the rigidity of the insertion part can be enhanced.

In the surgery system related to a still further aspect of the invention, the overtube has an endoscope insertion passage through which the endoscope is inserted so as to be movable forward and backward, a treatment tool insertion passage through which the treatment tool is inserted so as to be movable forward and backward, and a partition wall member having a partition wall between the endoscope insertion passage and the treatment tool insertion passage. The movable body is a ring body that is externally fitted to an outer peripheral part of the partition wall member, the endoscope holding part and the treatment tool holding part is provided inside the ring body. The movable body has an endoscope locking part to which the endoscope holding part is locked, and a treatment tool locking part to which the treatment tool holding part is locked, and has a sensing region where either the endoscope or the treatment tool is moved forward and backward in an interlocking manner with the forward and backward movement of the other. Accordingly, since the endoscope moves forward and backward with respect to the forward and backward movement operation in the sensing region, the range of an observation site that appears in an endoscopic image to be displayed on a monitor is continuously changed so as to follow the forward and backward movement of the treatment tool. As a result, since the size of images of observation sites other than a distal end site of the treatment tool that appears in the endoscopic image, and the size of the range of the observation site changes in accordance with the operation of the treatment tool, the operator can simply obtain a desired image.

In the surgery system related to a still further aspect of the invention, the endoscope holding part has a holding frame, and an annular elastic holder that is provided within the holding frame and elastically holds the held part, and is movable forward and backward along the endoscope insertion passage. The treatment tool holding part moves so as to be movable forward and backward along the treatment tool insertion passage. The endoscope locking part has a first restricting part that is provided at the ring body and restricts the forward and backward movement of the endoscope holding part with respect to the ring body in a first range. The first restricting part is engaged with the holding frame. The treatment tool locking part has a second restricting part that is provided at the ring body, restricts the forward and backward movement of the treatment tool holding part with respect to the ring body in a second range different from the first range. At least the holding frame, the ring body, and the first restricting part are made of metal. Accordingly, the movable body has the sensing region.

In the surgery system related to a still further aspect of the invention, the movable body has a non-sensing region where either the endoscope or the treatment tool is not moved forward and backward in an interlocking manner with the forward and backward movement of the other. Accordingly, since the endoscope does not move forward and backward with respect to the forward and backward movement operation thereof in the non-sensing region, the range of the observation site, such as the distal end site of the treatment tool or a body cavity inner site, to be displayed as the endoscopic image on the monitor does not vary, and the size of an image of the observation site can be prevented from fluctuating in accordance with minute displacement of the treatment tool. As a result, a sense of perspective can be suitably maintained, and a stable endoscopic image can be obtained.

An endoscope for achieving the object of the invention is an endoscope used in combination with an overtube that has a distal end, a proximal end, and a longitudinal axis and holds a treatment tool and an endoscope so as to be movable forward and backward in a direction of the longitudinal axis. The overtube has a metallic movable body that is provided within the overtube and is movable in the longitudinal axis direction inside the overtube, an endoscope holding part that is provided at the movable body and holds the endoscope, and a treatment tool holding part that is provided at the movable body and holds the treatment tool. The endoscope has an insertion part which is insertable into the overtube and has a distal end, a proximal end, and a longitudinal axis and is locked to the movable body by the endoscope holding part. The endoscope comprises a first insertion part that is provided on a distal end side of the insertion part, a second insertion part that is provided on a proximal end side of the first insertion part and has an external diameter larger than that of the first insertion part, and a held part that is provided from a distal end of the second insertion part toward a proximal end side thereof, is held by the endoscope holding part, and has at least a surface formed of an insulating member having an insulation property.

A surgery system and an endoscope of the invention can ensure insulation between an endoscope and a treatment tool even in a case where a movable body is formed of metal.

BRIEF DESCRIPTION OF THE DRAWINGS

FIG. 9 is an illustrative view for illustrating a non-sensing region of the coupling ring.

FIG. 17A is an illustrative view for illustrating holding of the endoscope insertion part by the endoscope fixture of the overtube.

FIG. 17B is an illustrative view for illustrating the holding of the endoscope insertion part by the endoscope fixture of the overtube together with FIG. 17A.

FIG. 21A is a cross sectional view of an endoscope insertion part of the endoscope in a still further Embodiment 2.

FIG. 21B is a cross sectional view of the endoscope insertion part of the endoscope provided with a tapered part in the still further Embodiment 2.

DESCRIPTION OF THE PREFERRED EMBODIMENTS

Preferred embodiments of the invention will be described below in detail according to the accompanying drawings. In addition, any of the drawings may illustrate main parts in an exaggerated manner for description, and may have dimensions different from actual dimensions.

[Overall Configuration of Surgery System]

Figure 1:
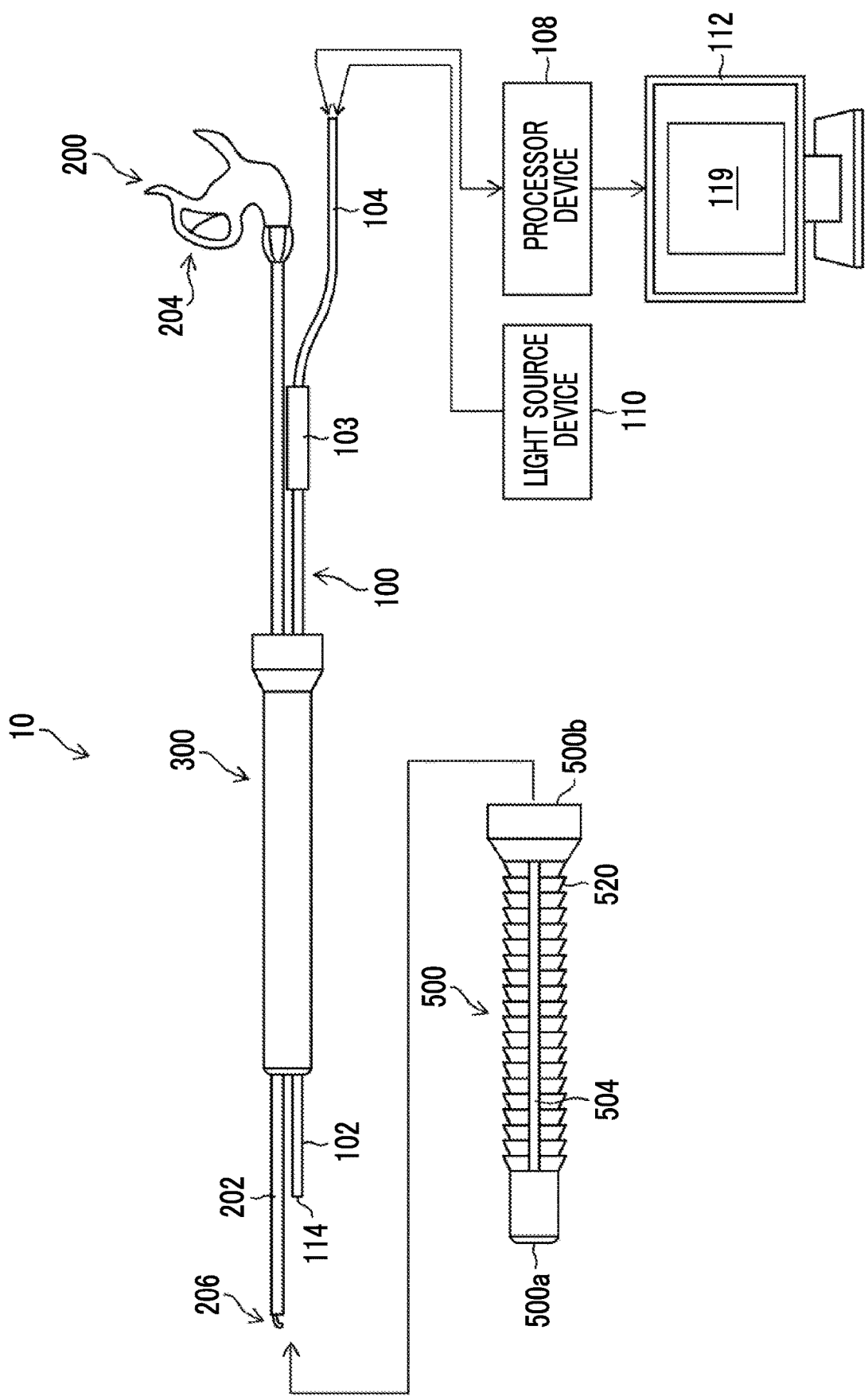
FIG. 1 is a schematic configuration view of a surgery system of the invention.

FIG. 1 is a schematic configuration view of a surgery system 10 of the invention. As illustrated in FIG. 1, the surgery system 10 includes an endoscope 100, a treatment tool 200, an overtube 300, and an outer sheath 500 (also referred to as a sheathing tube), and is used for observation, examination, and treatment within a body cavity of a patient.

The endoscope 100 is, for example, a rigid endoscope, such as a laparoscope, and is inserted into the body cavity to observe the inside of the body cavity. The endoscope 100 includes an elongated rigid endoscope insertion part 102 (equivalent to an insertion part of the endoscope of the invention) to be inserted into the body cavity, a connecting part 103 continuously provided at a proximal end part of the endoscope insertion part 102, and a flexible cord part 104 connected to the endoscope insertion part 102 by the connecting part 103. A connector (not illustrated) is provided at an end of the cord part 104 opposite to a side connected to the connecting part 103, and each of a processor device 108 and a light source device 110 is detachably connected to the cord part via the connector. Additionally, a monitor 112 is connected to the processor device 108 via a cable.

A distal end part of the endoscope insertion part 102 is provided with an observation part that observes the inside of the patient's body cavity. The observation part includes an observation window 116 (refer to FIG. 18) provided on a distal end surface 114 of the endoscope insertion part 102, an illumination unit and an observation optical system (not illustrated) that are provided behind the observation window 116, and a solid-state image pick-up element.

An exit end of a light guide (not illustrated) is disposed at the illumination unit. The light guide is inserted through the endoscope insertion part 102, the connecting part 103, and the cord part 104, extends up to the aforementioned connector, and is connected to the light source device 110. Accordingly, illumination light radiated from the light source device 110 is radiated from the illumination unit through the light guide to the front of the endoscope insertion part 102. Accordingly, the inside of the patient's body cavity is illuminated. In addition, the illumination unit may be provided behind the illumination window (not illustrated) provided on the distal end surface 114.

Subject light taken in from the observation window 116 is focused on an image pick-up surface of the solid-state image pick-up element by the observation optical system, and is converted into image pick-up signals by the solid-state image pick-up element. A signal cable (not illustrated) connected to the solid-state image pick-up element is inserted through the endoscope insertion part 102, the connecting part 103, and the cord part 104, extends up to the aforementioned connector, and is connected to the processor device 108. Accordingly, the processor device 108 displays an endoscopic image 119 on the monitor 112 on the basis of the image pick-up signals input from the solid-state image pick-up element.

The treatment tool 200 is, for example, an electric scalpel, and is inserted into the body cavity to treat an affected part within the body cavity. The treatment tool 200 includes an elongated treatment tool insertion part 202 to be inserted into the body cavity, an operating part 204 that is provided on a proximal end side of the treatment tool insertion part 202 and is gripped by an operator, and a treatment part 206 that is provided at a distal end of the treatment tool insertion part 202 and generates a high-frequency current by the operation of the operating part 204. In addition, since the structure of the electric scalpel is a well-known technique, a specific description thereof will be omitted.

Addition, the treatment tool 200 is not limited to the electric scalpel, and may be, for example, other treatment tools (particularly treatment tools that generates an electric current), such as forceps, a laser probe, a suture device, an electric scalpel, a needle holder, an ultrasonic device, or an aspirator.

The overtube 300 allows the endoscope insertion part 102 and the treatment tool insertion part 202 to be inserted thereinto from the proximal end side and delivered from the distal end side. By inserting the overtube 300 into a body wall, disposing a proximal end side of the overtube outside of the body, and disposing a distal end side of the overtube within the body cavity, the endoscope insertion part 102 and the treatment tool insertion part 202 are guided into the body cavity with one overtube 300. Additionally, although the overtube 300 will be described below in detail, the overtube 300 includes an interlocking function of moving the endoscope insertion part 102 and the treatment tool insertion part 202 forward and backward in an interlocking manner. Accordingly, for example, the endoscope insertion part 102 is capable of being moved forward and backward by the forward and backward movement operation of only the treatment tool insertion part 202, and a suitable endoscopic image 119 is obtained without performing the forward and backward movement operation of the endoscope insertion part 102.

The outer sheath 500 is formed in a tubular shape, and has a distal end opening 500a and a proximal end opening 500b, and an insertion passage (not illustrated) through which the overtube 300 is rotatably inserted around the longitudinal axis toward the distal end opening 500a from the proximal end opening 500b. A number of lateral grooves 520 in the circumferential direction of the outer sheath 500 are provided at an outer peripheral part of the outer sheath 500, and longitudinal grooves 504 in a longitudinal axis direction are provided at a plurality of points in the circumferential direction of the outer sheath 500. Accordingly, in a state where the overtube 300 is inserted into the body wall together with the outer sheath 500, each lateral groove 520 restricts the forward and backward movement of the outer sheath 500 with respect to the body wall, and each longitudinal groove 504 restricts the circumferential rotation of the outer sheath 500 with respect to the body wall. Therefore, unintended rotation and forward and backward movement of the overtube 300 inserted through the outer sheath 500 with respect to the body wall are prevented. For this reason, a situation in which the position of a distal end of the endoscope insertion part 102 fluctuates and an observation visual field unintentionally fluctuates is prevented.

[Configuration of Overtube]

Figure 2:
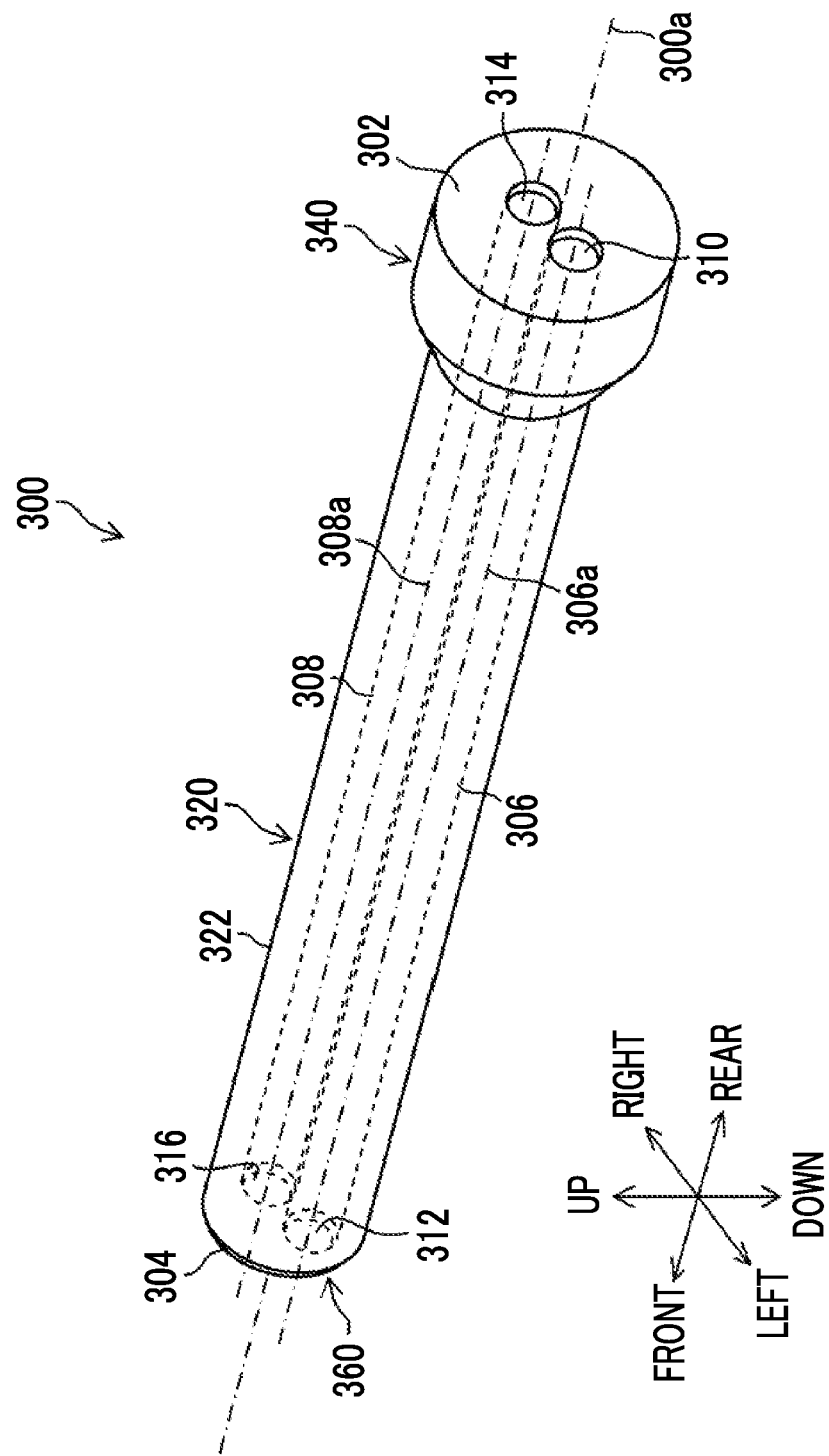
FIG. 2 is an external perspective view of an overtube.

FIG. 2 is an external perspective view of the overtube 300. As illustrated in FIG. 2, the entire overtube 300 has an elongated cylindrical shape and has a distal end, a proximal end, and a longitudinal axis 300a. The overtube 300 has an endoscope insertion passage 306 through which the endoscope insertion part 102 is inserted so as to be movable forward and backward along the longitudinal axis 300a, and a treatment tool insertion passage 308 through which the treatment tool insertion part 202 of the treatment tool 200 is inserted so as to be movable forward and backward along the longitudinal axis 300a. The endoscope insertion passage 306 and the treatment tool insertion passage 308 are disposed parallel to each other and are disposed parallel to the longitudinal axis 300a.

Reference sign "306a" in the drawing designates an endoscope insertion axis equivalent to a central axis of the endoscope insertion passage 306. Additionally, reference sign "308a" in the drawing designates a treatment tool insertion axis equivalent to a central axis of the treatment tool insertion passage 308. In the present embodiment, although the longitudinal axis 300a, the endoscope insertion axis 306a, and the treatment tool insertion axis 308a are disposed on the same plane, these axes are not necessarily disposed on the same plane.

In addition, regarding the position and orientation of a space where the overtube 300 is disposed, terms called "forward", "backward", "left", "right", "up", and "down" are used with the orientation from a proximal end surface 302 in a direction along the longitudinal axis 300a to a distal end surface 304 defined as the forward and with the orientation from the longitudinal axis 300a to the treatment tool insertion axis 308a defined as the right.

The proximal end surface 302 of the overtube 300 is provided with a first proximal end opening 310 that is a proximal end opening that allows the endoscope insertion part 102 to be inserted into the endoscope insertion passage 306 therethrough, and a second proximal end opening 314 that is proximal end opening that allows the treatment tool insertion part 202 to be inserted into the treatment tool insertion passage 308 therethrough. Additionally, the distal end surface 304 of the overtube 300 is provided with a first distal end opening 312 that is a distal end opening that allows the endoscope insertion part 102 inserted into the endoscope insertion passage 306 to be delivered forward therethrough, and a second distal end opening 316 that is a distal end opening that allows the treatment tool insertion part 202 inserted into the treatment tool insertion passage 308 to be delivered forward therethrough. That is, the endoscope insertion passage 306 allows the first distal end opening 312 and the first proximal end opening 310 to communicate with each other, and the treatment tool insertion passage 308 allows the second distal end opening 316 and the second proximal end opening 314 to communicate with each other.

The overtube 300 is constituted of a long tubular overtube part 320 having a shape extending along the longitudinal axis 300a, a proximal end cap 340 that is attached to a proximal end of the long tubular overtube part 320, and a distal end cap 360 that is attached to a distal end of the long tubular overtube part 320.

The proximal end cap 340 is formed in a columnar shape of which the diameter is made larger than the external diameter of the long tubular overtube part 320 using rigid resins, metals, or the like, and a rear end surface thereof constitutes the aforementioned proximal end surface 302. Additionally, the distal end cap 360 is formed of rigid resins, metals, or the like, and a front end surface thereof constitutes the aforementioned distal end surface 304.

The long tubular overtube part 320 has a long tubular body 322 that is formed in an elongated cylindrical shape having the longitudinal axis 300a as central axis using rigid resins, metals, or the like. Additionally, the long tubular overtube part 320 has a slider 400 (refer to FIG. 3) that is an interlocking mechanism that moves the endoscope insertion passage 306 and the treatment tool insertion passage 308, and the endoscope insertion part 102 and the treatment tool insertion part 202 forward and backward in an interlocking manner in a direction of the longitudinal axis 300a (a longitudinal axis direction) within the long tubular body 322.

Figure 3A:
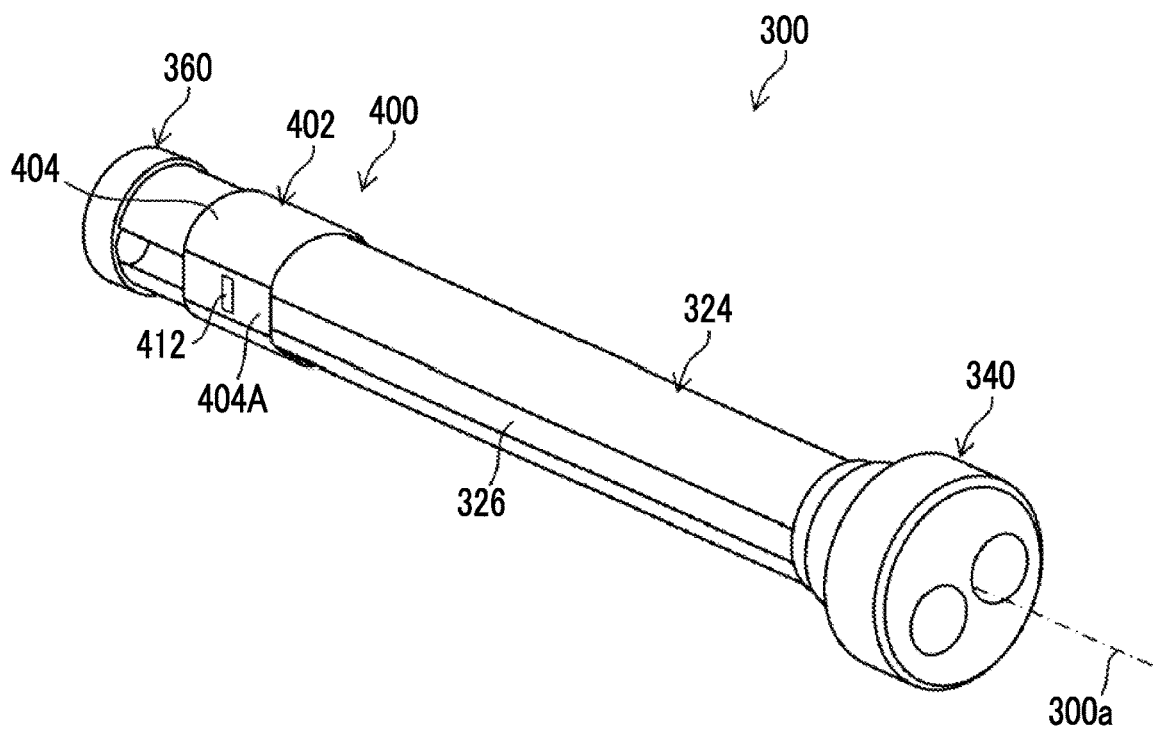
FIG. 3A is an external perspective view illustrating a long tubular overtube part with a long tubular body omitted.
Figure 3B:
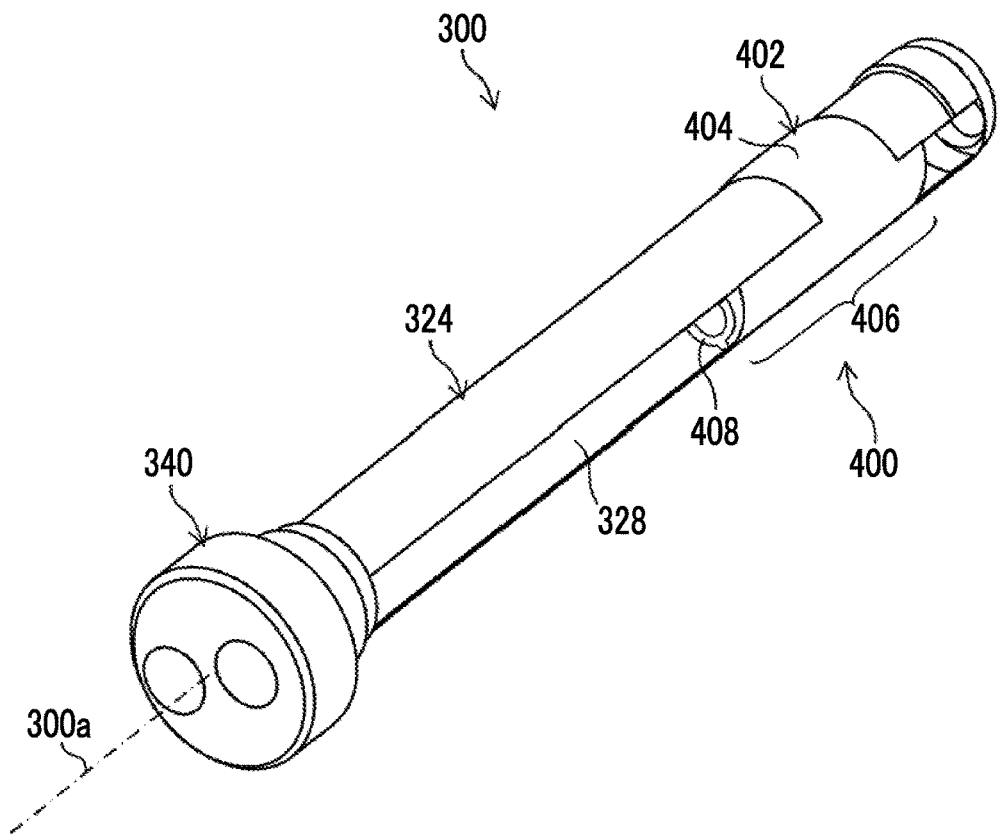
FIG. 3B is an external perspective view of the long tubular overtube part with the long tubular body omitted, as seen from a direction different from FIG. 3A.

FIGS. 3A and 3B are external perspective views illustrating the long tubular overtube part 320 with the long tubular body 322 omitted. As illustrated in FIGS. 3A and 3B, a substantially columnar partition wall member 324, which extends along the longitudinal axis 300a, and the slider 400, which is guided by the partition wall member 324 and is supported so as to be movable forward and backward in a forward-backward direction are provided within the long tubular body 322.

Figure 4:
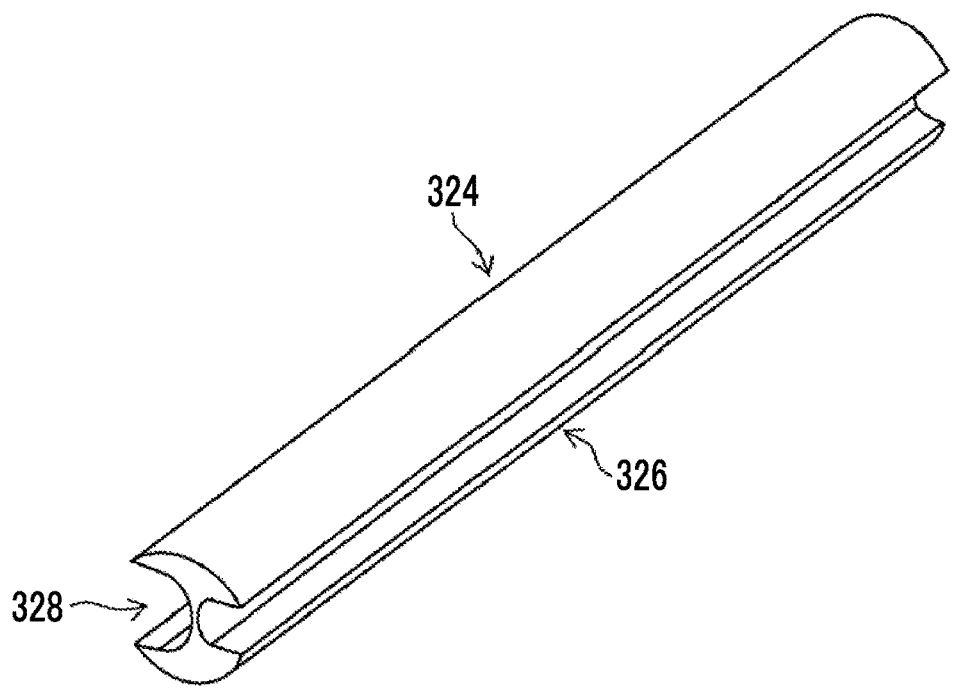
FIG. 4 is an external perspective view of a partition wall member.

FIG. 4 is an external perspective view of the partition wall member 324. As illustrated in FIG. 4, the partition wall member 324 is a solid insulator formed of, for example, resin and extends from the proximal end cap 340 to the distal end cap 360 inside the long tubular body 322. An endoscope guide groove 326 and a treatment tool guide groove 328, which extend parallel to the longitudinal axis 300a from a proximal end of the partition wall member 324 to a distal end thereof, are respectively formed on a side surface of the partition wall member 324. The endoscope guide groove 326 forms a portion of the aforementioned endoscope insertion passage 306, and the treatment tool guide groove 328 forms a portion of the aforementioned treatment tool insertion passage 308. Additionally, the partition wall member 324 forms a partition wall between the endoscope insertion passage 306 and the treatment tool insertion passage 308.

By virtue of the partition wall member 324, the endoscope insertion part 102 and the treatment tool insertion part 202 inserted into the overtube 300 reliably proceed through the regions of the endoscope insertion passage 306 and the treatment tool insertion passage 308 corresponding thereto without falling out of the insertion passages, respectively. For this reason, the task of inserting the endoscope insertion part 102 and the treatment tool insertion part 202 into the overtube 300 becomes easy. Additionally, the contact between the endoscope insertion part 102 and the treatment tool insertion part 202 inside the overtube 300 is prevented.

Returning to FIGS. 3A and 3B, the slider 400 is externally fitted to an outer peripheral part of the partition wall member 324 inside the long tubular body 322, and is a ring-shaped movable body that is movable forward and backward in the direction of the longitudinal axis 300a with respect to the partition wall member 324. That is, the slider 400 is equivalent to a movable body of the invention.

Figure 5:
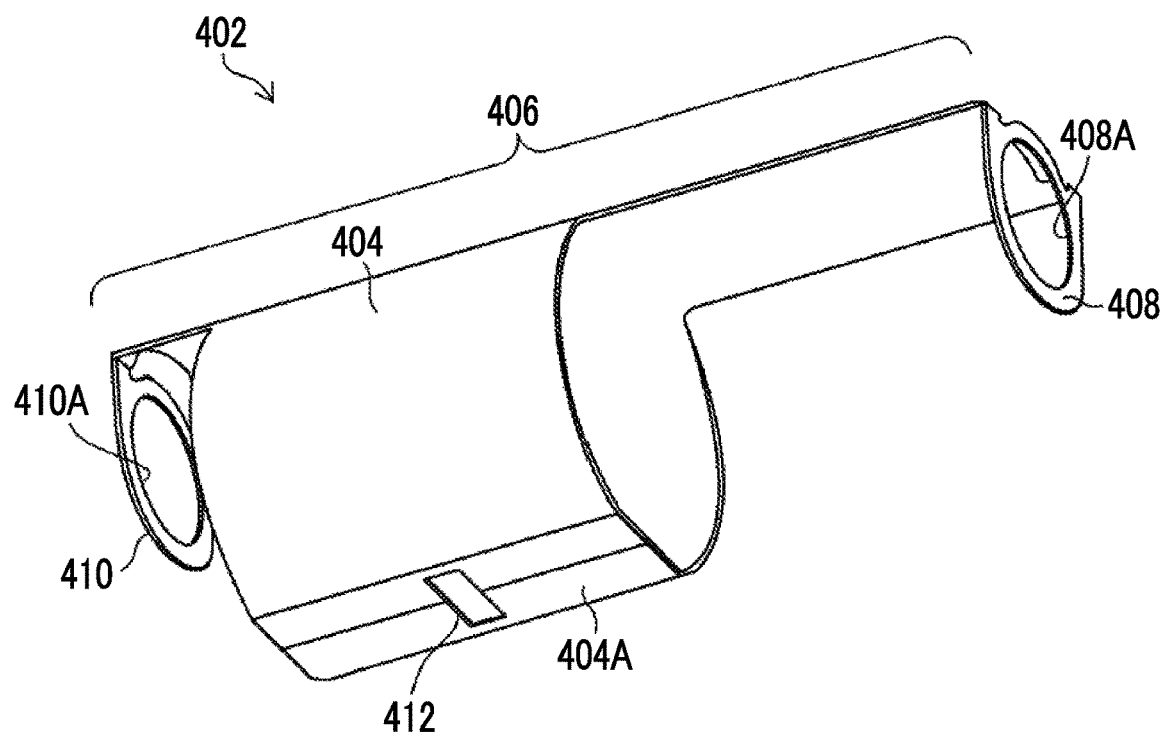
FIG. 5 is an external perspective view of a coupling ring that constitutes a portion of a slider.
Figure 6:
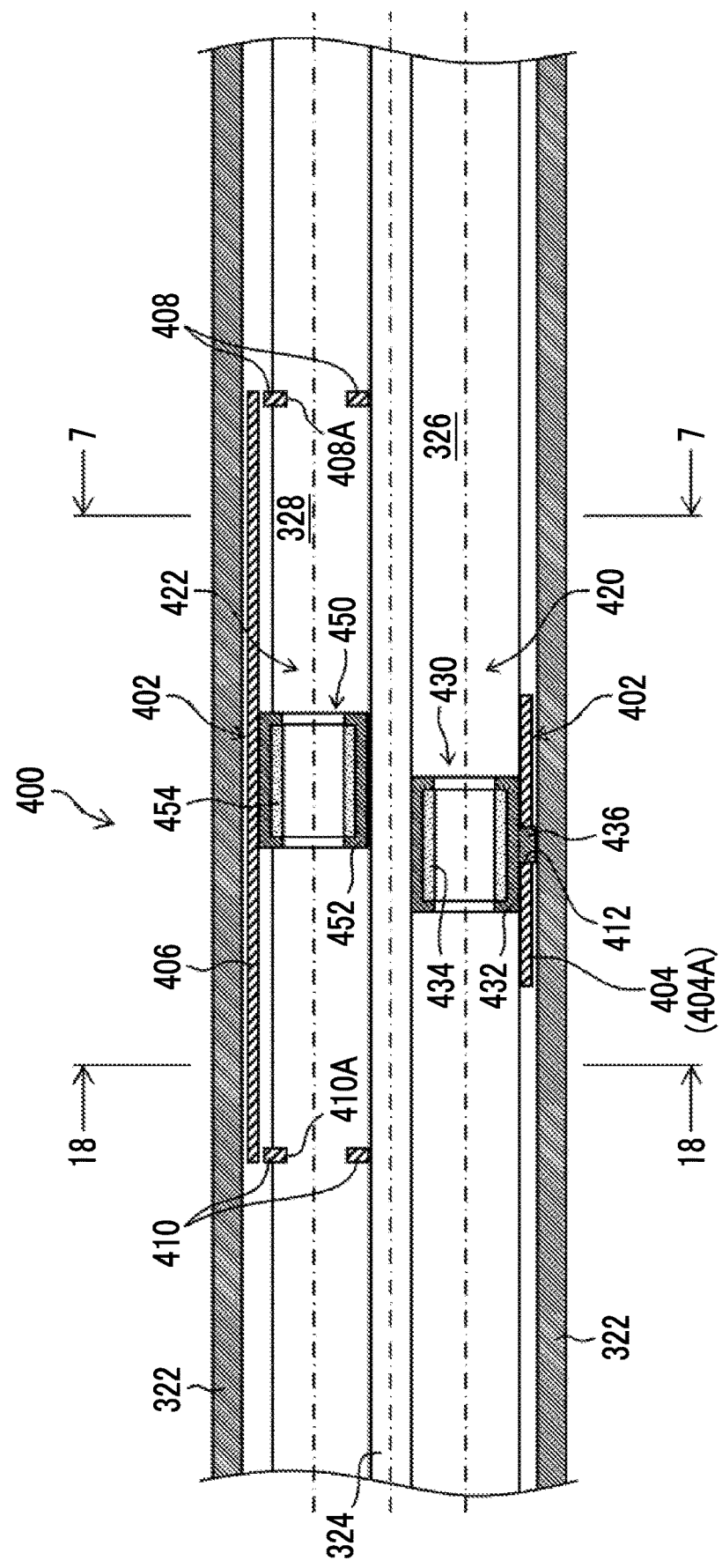
FIG. 6 is a cross sectional view of the overtube and the slider cut in a horizontal plane, including a longitudinal axis, which is orthogonal to an upward-downward direction.

FIG. 5 is an external perspective view of a coupling ring 402 that constitutes a portion of the slider 400. Additionally, FIG. 6 is a cross sectional view of the overtube 300 and the slider 400 cut in the horizontal plane, including the longitudinal axis 300a, which is orthogonal to an upward-downward direction.

As illustrated in FIGS. 3A, 3B, 5, and 6, the slider 400 has an endoscope coupling part 420 that is disposed inside the endoscope guide groove 326, a treatment tool coupling part 422 that is disposed inside the treatment tool guide groove 328, and the metallic coupling ring 402 that integrally interlocks the endoscope coupling part 420 and the treatment tool coupling part 422 with each other. In addition, the metallic movable body of the invention refers to the coupling ring 402 in the slider 400 being made of at least metals.

The coupling ring 402 is equivalent to a ring body of the invention, and has a tubular ring part 404 that surrounds an outer periphery of the partition wall member 324 in the circumferential direction, and an arm part 406. The ring part 404 is in contact with or close contact with portions other than the endoscope guide groove 326 and the treatment tool guide groove 328 in an outer peripheral surface of the partition wall member 324. Additionally, the arm part 406 extends in the forward-backward direction along the treatment tool guide groove 328 from the portion of the ring part 404 that faces the treatment tool guide groove 328.

A rear restriction end 408 and a front restriction end 410 that are disposed to be inserted into the treatment tool guide groove 328 are respectively provided at a distal end and a proximal end of the arm part 406. The rear restriction end 408 and the front restriction end 410 are respectively provided with openings 408A and 410A through which the treatment tool insertion part 202 is inserted. Also, the rear restriction end 408 and the front restriction end 410 restrict the forward and backward movement of the treatment tool coupling part 422 (a treatment tool fixture 450 to be described below), which is disposed inside the treatment tool guide groove 328, in the forward-backward direction therebetween. That is, the rear restriction end 408 and the front restriction end 410 function as a treatment tool locking part and a second restricting part of the invention.

A flat first engaging part 404A, which is parallel to an opening of the endoscope guide groove 326 and extends in the forward-backward direction, is formed at the portion of the ring part 404 that faces the endoscope guide groove 326. The rotation of the coupling ring 402 around of the longitudinal axis 300a (hereinafter abbreviated as "around the longitudinal axis") with respect to the partition wall member 324 is restricted by the first engaging part 404A and the aforementioned rear restriction end 408 and front restriction end 410. Additionally, an engaging hole 412 to be described below is formed in the first engaging part 404A.

Also, the coupling ring 402 is supported by the partition wall member 324 so as to be movable forward and backward in the forward-backward direction, and is supported by the partition wall member 324 in a state where the movement of the coupling ring in the upward-downward direction and the rotation of the coupling ring in all directions (direction around three axes including a forward-backward axis, a leftward-rightward axis, and an upward-downward axis) are restricted (a state where at least the rotation of the coupling ring around at least the longitudinal axis is impossible). Additionally, the coupling ring 402 moves forward and backward within a movable range having a position, where the rear restriction end 408 of the coupling ring 402 abuts against the proximal end cap 340, as a rear end, and having a position, where the front restriction end 410 of the coupling ring 402 abuts against the distal end cap 360, as a front end.

Figure 7:
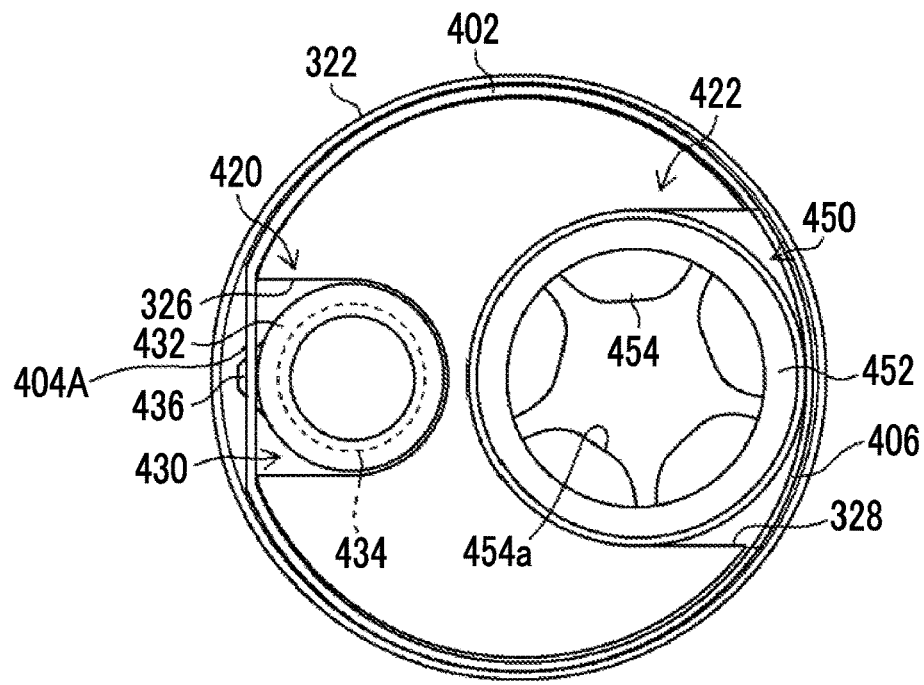
FIG. 7 is a cross sectional view taken along line "7-7" in FIG. 6.
Figure 8A:
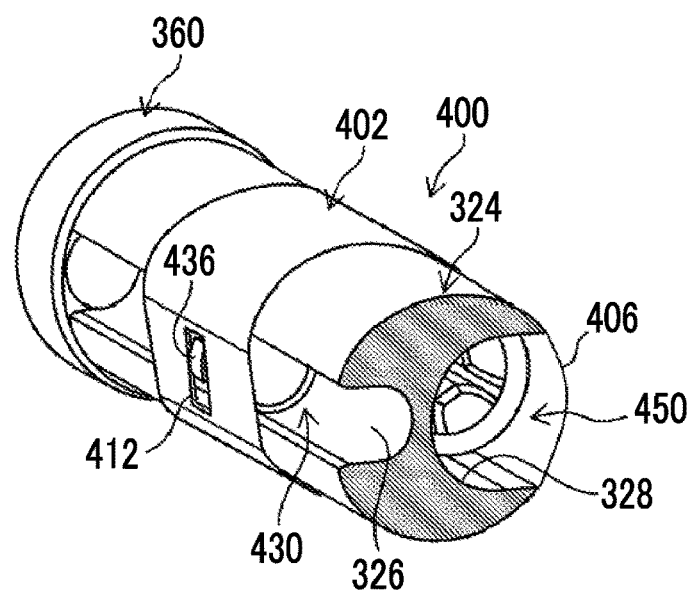
FIG. 8A is a perspective view illustrating the overtube cut in a plane perpendicular to the longitudinal axis at a position intersecting an arm part extending further toward a proximal end side than a ring part in FIG. 3A.
Figure 8B:
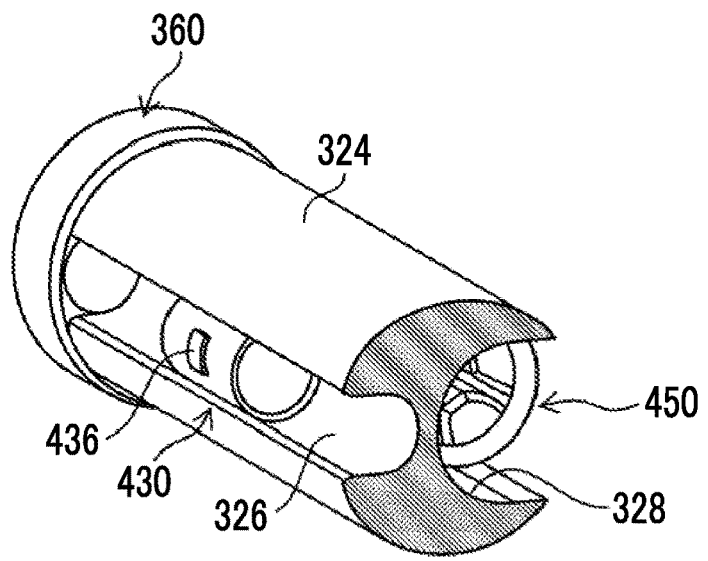
FIG. 8B is a perspective view illustrating FIG. 8A with the coupling ring omitted.
Figure 8C:
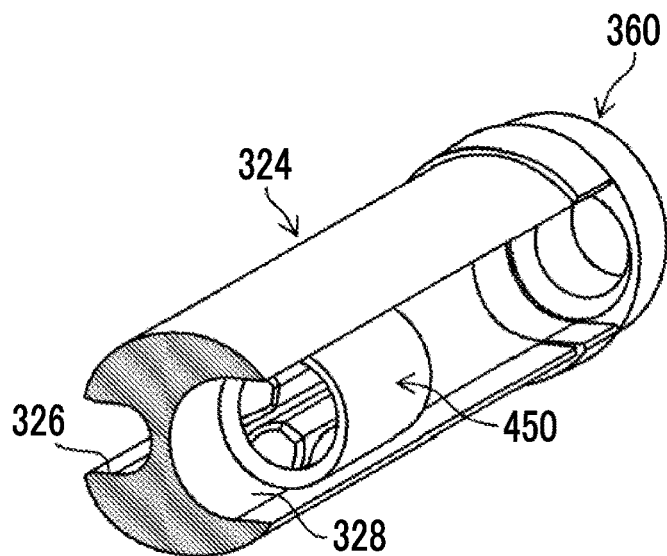
FIG. 8C is a perspective view of the overtube of FIG. 8B as seen from a different direction.

FIG. 7 is a cross sectional view taken along line "7-7" in FIG. 6. FIG. 8A is a perspective view illustrating the overtube 300 cut in a plane perpendicular to the longitudinal axis 300a at a position intersecting the arm part 406 extending further toward the proximal end side than the ring part 404 in FIG. 3A. FIG. 8B is a perspective view illustrating FIG. 8A with the coupling ring 402 omitted. FIG. 8C is a perspective view of the overtube 300 of FIG. 8B as seen from a different direction.

As illustrated in FIGS. 6, 7, and 8A to 8C, the endoscope coupling part 420 is disposed within the endoscope guide groove 326, and is coupled (engaged) with the endoscope insertion part 102 inserted into the endoscope guide groove 326. Additionally, the treatment tool coupling part 422 is disposed within the treatment tool guide groove 328, and is coupled (engaged) with the treatment tool insertion part 202 inserted into the treatment tool guide groove 328.

The endoscope coupling part 420 has an endoscope fixture 430 that is disposed inside the endoscope guide groove 326, and is movable forward and backward in the forward-backward direction along the endoscope insertion passage 306 formed in the endoscope guide groove 326. The endoscope fixture 430 is equivalent to an endoscope holding part of the invention, and holds the endoscope 100 (endoscope insertion part 102) within the slider 400. The endoscope fixture 430 is constituted of a tubular metallic holding frame 432 that approaches or comes into contact with an inner wall surface of the endoscope guide groove 326, and a tubular (annular) endoscope elastic holder 434, such as O-ring, which is fixed inside the holding frame 432 and formed of elastic materials, such as elastic rubber.

The holding frame 432 has a shape such that the movement (rotation) thereof is impossible in the direction around the axis inside the endoscope guide groove 326, and the endoscope fixture 430 is allowed only to move forward and backward in the forward-backward direction within the endoscope guide groove 326. Additionally, the holding frame 432 has a cross section of an inner peripheral surface in the forward-backward direction formed in a recessed shape over an entire inner periphery thereof (refer to FIG. 16). The endoscope elastic holder 434 is fitted and fixed to a recess of the inner peripheral surface of the holding frame 432. Accordingly, the endoscope elastic holder 434 contains oil. Thus, even in a case where the endoscope elastic holder 434 cannot be fixed to the holding frame 432 using an adhesive, the endoscope elastic holder 434 can be fixed inside the holding frame 432. For this reason, a portion (an end part in the forward-backward direction) of the holding frame 432 comes into contact with an outer peripheral surface of the endoscope insertion part 102 (refer to FIG. 16).

An outer peripheral surface of the holding frame 432 is provided with a protrusion 436 that protrudes toward the outside of an opening of the endoscope guide groove 326 at a position that faces the opening. The protrusion 436 is inserted through the engaging hole 412 formed in the first engaging part 404A, and is locked in the forward-backward direction. That is, since the first engaging part 404A having the engaging hole 412 is engaged with the holding frame 432 via the protrusion 436, the first engaging part 404A functions as an endoscope locking part and a first restricting part of the invention. Accordingly, the relative forward and backward movement of the endoscope fixture 430 in the forward-backward direction with respect to the coupling ring 402 is restricted. Therefore, the coupling ring 402 and the endoscope fixture 430 integrally move forward and backward in the forward-backward direction.

The endoscope elastic holder 434 is equivalent to an annular elastic holder of the invention, and has an endoscope holding surface 434a (refer to FIG. 17A) that is brought into pressure contact (engaged) with an outer peripheral surface of the endoscope insertion part 102 inserted therethrough to elastically hold the endoscope insertion part 102. Accordingly, an endoscope longitudinal axis 100a (refer to FIG. 13), which is a longitudinal axis of the endoscope insertion part 102, is disposed substantially coaxially with the endoscope insertion axis 306a. Since the endoscope holding surface 434a is brought into pressure contact with the outer peripheral surface of the endoscope insertion part 102 due to an elastic force, the endoscope holding surface 434a allows the circumferential rotation of the endoscope 100 centered on the endoscope longitudinal axis 100a. Additionally, the endoscope elastic holder 434 is able to randomly adjust the holding position of the endoscope insertion part 102 in the forward-backward direction.

The treatment tool coupling part 422 has the treatment tool fixture 450 that is disposed between the rear restriction end 408 of the aforementioned arm part 406, and the front restriction end 410, inside the treatment tool guide groove 328. The treatment tool fixture 450 is equivalent to a treatment tool holding part of the invention, and holds the treatment tool 200 (treatment tool insertion part 202) within the slider 400. In other words, the treatment tool 200 is locked to the slider 400 with the treatment tool fixture 450. The treatment tool fixture 450 is movable forward and backward in the forward-backward direction along the treatment tool guide groove 328 between the rear restriction end 408 and the front restriction end 410.

The treatment tool fixture 450 is constituted of a tubular metallic frame 452 that approaches or comes into contact with an inner wall surface of the treatment tool guide groove 328, and a tubular (annular) treatment tool elastic holder 454, such as O-ring, which is fixed inside the frame 452 and formed of elastic materials, such as elastic rubber. In addition, an inner peripheral surface of the treatment tool elastic holder 454 is formed in a shape such that irregularities are repeated in the circumferential direction so as to be appropriately engageable with even treatment tool insertion parts 202 having a plurality of types of different diameters.

The treatment tool elastic holder 454 has a treatment tool holding surface 454a that is brought into pressure contact (engaged) with an outer peripheral surface of the treatment tool insertion part 202 inserted therethrough to elastically hold the treatment tool insertion part 202. Accordingly, the central axis (longitudinal axis) of the treatment tool insertion part 202 is disposed substantially coaxially with the treatment tool insertion axis 308a. Since the treatment tool holding surface 454a is brought into pressure contact with the outer peripheral surface of the treatment tool insertion part 202 due to an elastic force, the holding position of the treatment tool insertion part 202 in the forward-backward direction can be randomly adjusted by the treatment tool holding surface 454a.

The treatment tool fixture 450 also integrally moves forward and backward in an interlocking manner with the forward and backward movement of the treatment tool insertion part 202 in the forward-backward direction (axial direction). In this case, the treatment tool fixture 450 is movable forward and backward in the forward-backward direction along the treatment tool guide groove 328 between the rear restriction end 408 and the front restriction end 410, as mentioned above. That is, the arm part 406 allows the forward and backward movement of the treatment tool fixture 450 in the forward-backward direction with respect to the coupling ring 402 in a range from a position where the treatment tool fixture 450 abuts against the rear restriction end 408 to a position where the treatment tool fixture 450 abuts against the front restriction end 410, and restricts the treatment tool fixture 450 in that range.

Additionally, the treatment tool fixture 450 also rotates inside the treatment tool guide groove 328 in an interlocking manner with the rotation of the treatment tool insertion part 202 around the longitudinal axis thereof.

FIG. 9 is an illustrative view for illustrating a non-sensing region of the coupling ring 402. As illustrated in FIG. 9, in a case where a range where the endoscope fixture 430 is movable forward and backward with respect to the coupling ring 402 is defined as a first range and a range where the treatment tool fixture 450 is movable forward and backward with respect to the coupling ring 402 is defined as a second range, the first range becomes zero because the forward and backward movement of the endoscope fixture 430 in the forward-backward direction with respect to the first engaging part 404A of the coupling ring 402 is restricted as described above. In contrast, the second range is a range between the rear restriction end 408 and the front restriction end 410 as mentioned above. Accordingly, the coupling ring 402 has a non-sensing region where either the treatment tool fixture 450 or the endoscope fixture 430 is not moved forward and backward in an interlocking manner with the forward and backward movement of the other of the treatment tool fixture 450 and the endoscope fixture 430.

Since the endoscope 100 does not move forward and backward with respect to the forward and backward movement operation of the treatment tool in the non-sensing region (forward and backward movement in a range where the treatment tool fixture 450 and the rear restriction end 408 or the front restriction end 410 do not abut against each other), the range of an observation site, such as a distal end site of the treatment tool 200 and a body cavity inner site, to be displayed on the monitor 112 as an endoscopic image 119 does not vary, and the size of an image of the observation site can be prevented from fluctuating in accordance with minute displacement of the treatment tool 200. Accordingly, a sense of perspective can be suitably maintained, and a stable endoscopic image 119 can be obtained.

Figure 10A:
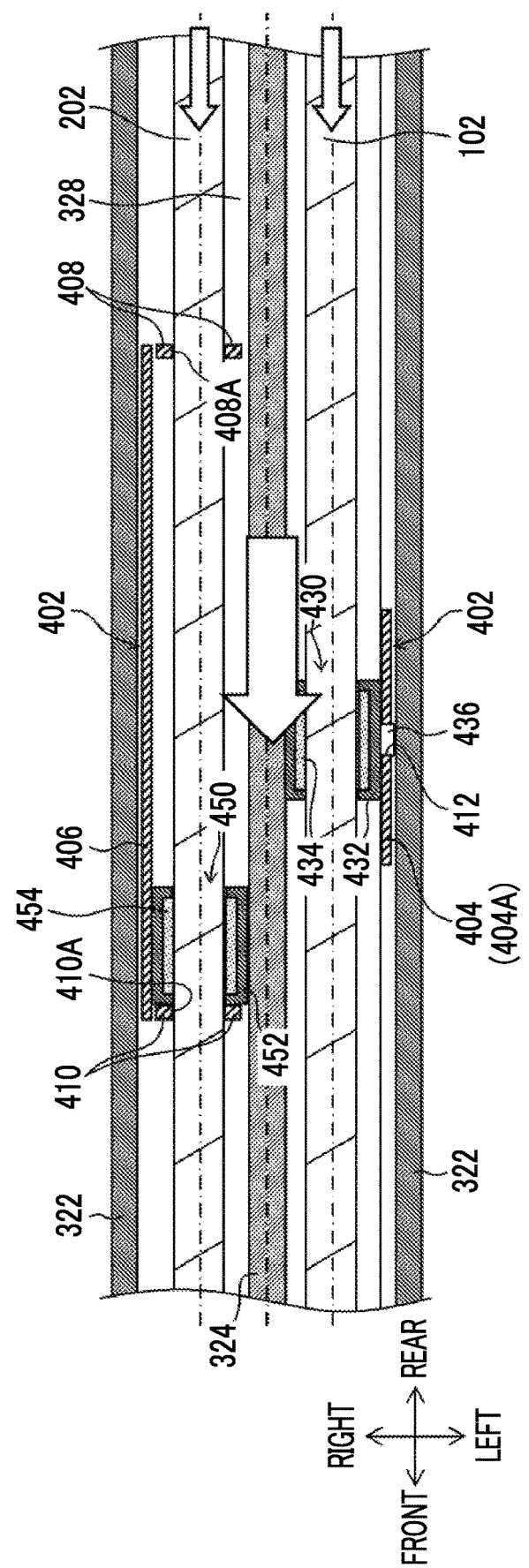
FIG. 10A is an illustrative view for illustrating a sensing region of the coupling ring.
Figure 10B:
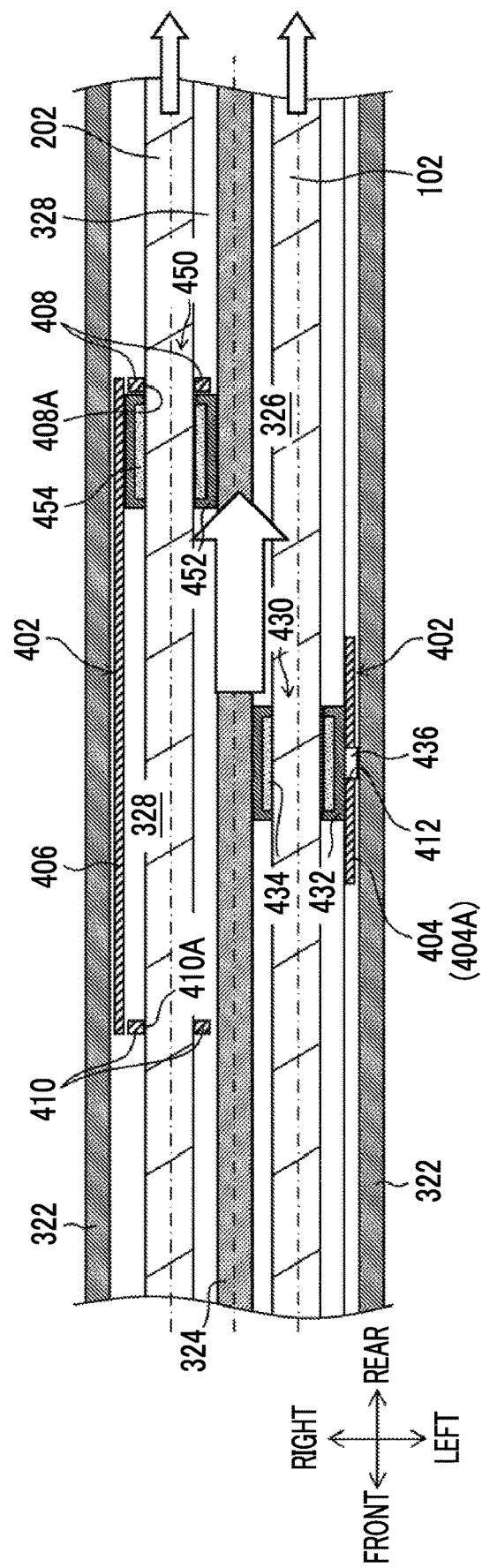
FIG. 10B is an illustrative view for illustrating the sensing region of the coupling ring together with FIG. 10A.

FIGS. 10A and 10B are illustrative views for describing a sensing region of the coupling ring 402. As illustrated in FIGS. 10A and 10B, in a case where the treatment tool fixture 450 has moved forward and backward in the forward-backward direction or in a case where the coupling ring 402 has moved forward and backward in the forward-backward direction together with the endoscope fixture 430, the treatment tool fixture 450 abuts against the rear restriction end 408 or the front restriction end 410. In this state, the coupling ring 402 has a sensing region where either the endoscope fixture 430 or the treatment tool fixture 450 is moved forward and backward movement in an interlocking manner with respect to the forward and backward movement (the forward and backward movement in a direction in which the treatment tool fixture 450 and the rear restriction end 408 or the front restriction end 410 are not spaced apart from each other) of other of the endoscope fixture 430 and the treatment tool fixture 450.

Since the endoscope 100 moves forward and backward with respect to the forward and backward movement operation in the sensing region, the range of the observation site that appears in an endoscopic image 119 to be displayed on the monitor 112 is continuously changed so as to follow the forward and backward movement of the treatment tool 200. Accordingly, since the size of images of observation sites other than the distal end site of the treatment tool 200 that appears in the endoscopic image according to the operation of the treatment tool 200, and the size of the range of the observation site changes, the surgeon can simply obtain a desired image.

In this way, the slider 400 has the non-sensing region where the forward and backward movement of either the endoscope insertion part 102 coupled to the endoscope fixture 430 or the treatment tool insertion part 202 coupled to the treatment tool fixture 450 in the forward-backward direction (axial direction) does not interlock with the forward and backward movement of the other and the sensing region where either the endoscope insertion part 102 or the treatment tool insertion part 202 is moved forward and backward in an interlocking manner with the forward and backward movement of the other. That is, the endoscope insertion part 102 is adapted to interlock with the forward and backward movement of the treatment tool insertion part 202 in the axial direction with play by the slider 400.

In addition, although the first range where the endoscope fixture 430 is movable forward and backward with respect to the coupling ring 402 is zero in the present embodiment, the forward and backward movement of the endoscope fixture 430 together with the treatment tool fixture 450 with respect to the coupling ring 402 or instead of the treatment tool fixture 450 may be allowed, and the first range may have a magnitude other than zero. Namely, a configuration may be adopted in which the forward and backward movement of at least one of the endoscope fixture 430 and the treatment tool fixture 450 with respect to the coupling ring 402 is allowed.

Additionally, in a case where the forward and backward movement of the endoscope fixture 430 with respect to the coupling ring 402 is allowed, it is possible to adopt a form in which the range, in the forward-backward direction, of the engaging hole 412 of the first engaging part 404A to be engaged with the protrusion 436 of the endoscope fixture 430 is increased. Accordingly, the endoscope fixture 430 can be made movable forward and backward with respect to the coupling ring 402 with the length range of the engaging hole 412 in the forward-backward direction as the first range. Moreover, the endoscope fixture 430 can be made movable forward and backward with respect to the coupling ring 402 using the same configuration as the rear restriction end 408 and the front restriction end 410 of the arm part 406 with respect to the treatment tool fixture 450.

Additionally, the endoscope fixture 430 may be rotatable around the endoscope insertion axis 306a within the endoscope insertion passage 306. In that case, the configuration of the arm part 406 of the coupling ring 402 with respect to the treatment tool fixture 450 can be adopted for the endoscope fixture 430.

In the above embodiment, although the endoscope insertion passage 306 (endoscope insertion axis 306a) and the treatment tool insertion passage 308 (treatment tool insertion axis 308a) are parallel to the longitudinal axis 300a, these axes may not be necessarily parallel to each other.

For example, the treatment tool insertion passage 308 may be disposed parallel to the longitudinal axis 300a, and the endoscope insertion passage 306 may be disposed obliquely with respect to the longitudinal axis 300a. In this case, since the endoscope fixture 430 moves also in the upward-downward direction with respect to the partition wall member 324 and the coupling ring 402 together with the forward and backward movement thereof in the forward-backward direction, the protrusion 436 formed on the outer peripheral part of the endoscope fixture 430 also moves in the upward-downward direction with respect to the coupling ring 402 in accordance with the position of the endoscope fixture 430 in the forward-backward direction. Thus, the engaging hole 412 is formed as an elongated hole extending in the circumferential direction (upward-downward direction) within the range of the first engaging part 404A or beyond this range.

Figure 11:
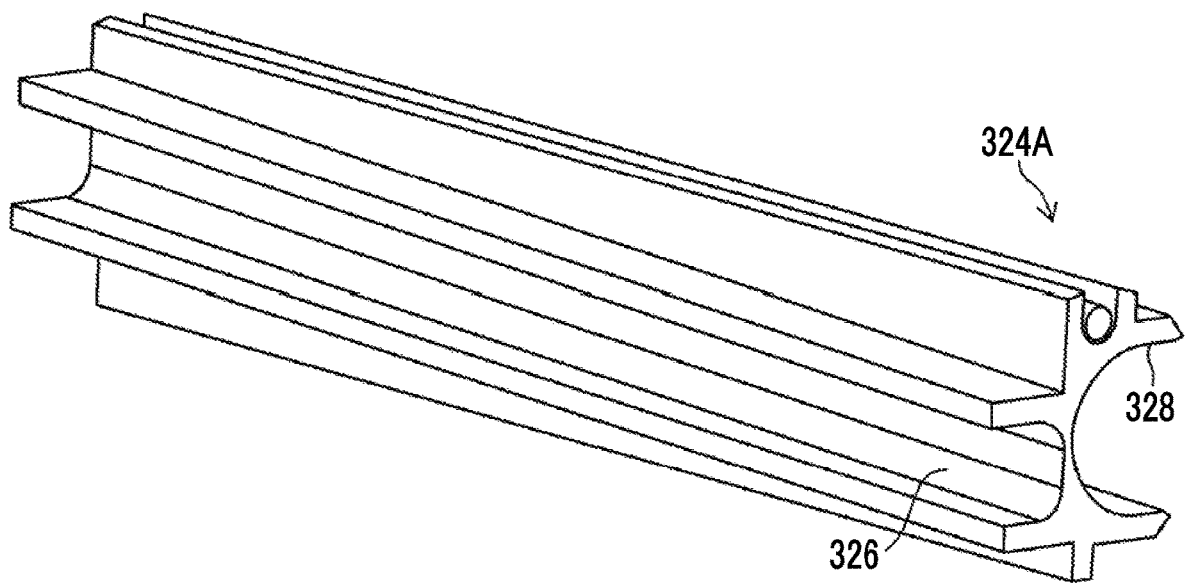
FIG. 11 is an external perspective view of a partition wall member of another embodiment.

In the above embodiment, the partition wall member 324 is formed basically in a columnar shape. However, the partition wall member 324 may form a partition wall at least between the endoscope insertion passage 306 and the treatment tool insertion passage 308 and the partition wall member 324 may not necessarily be formed basically in a columnar shape. Additionally, for example, almost all regions other than the endoscope insertion passage 306 and the treatment tool insertion passage 308 may be made hollow as in a partition wall member 324A illustrated in FIG. 11. FIG. 11 is an external perspective view of the partition wall member 324A of another embodiment.

Figure 12:
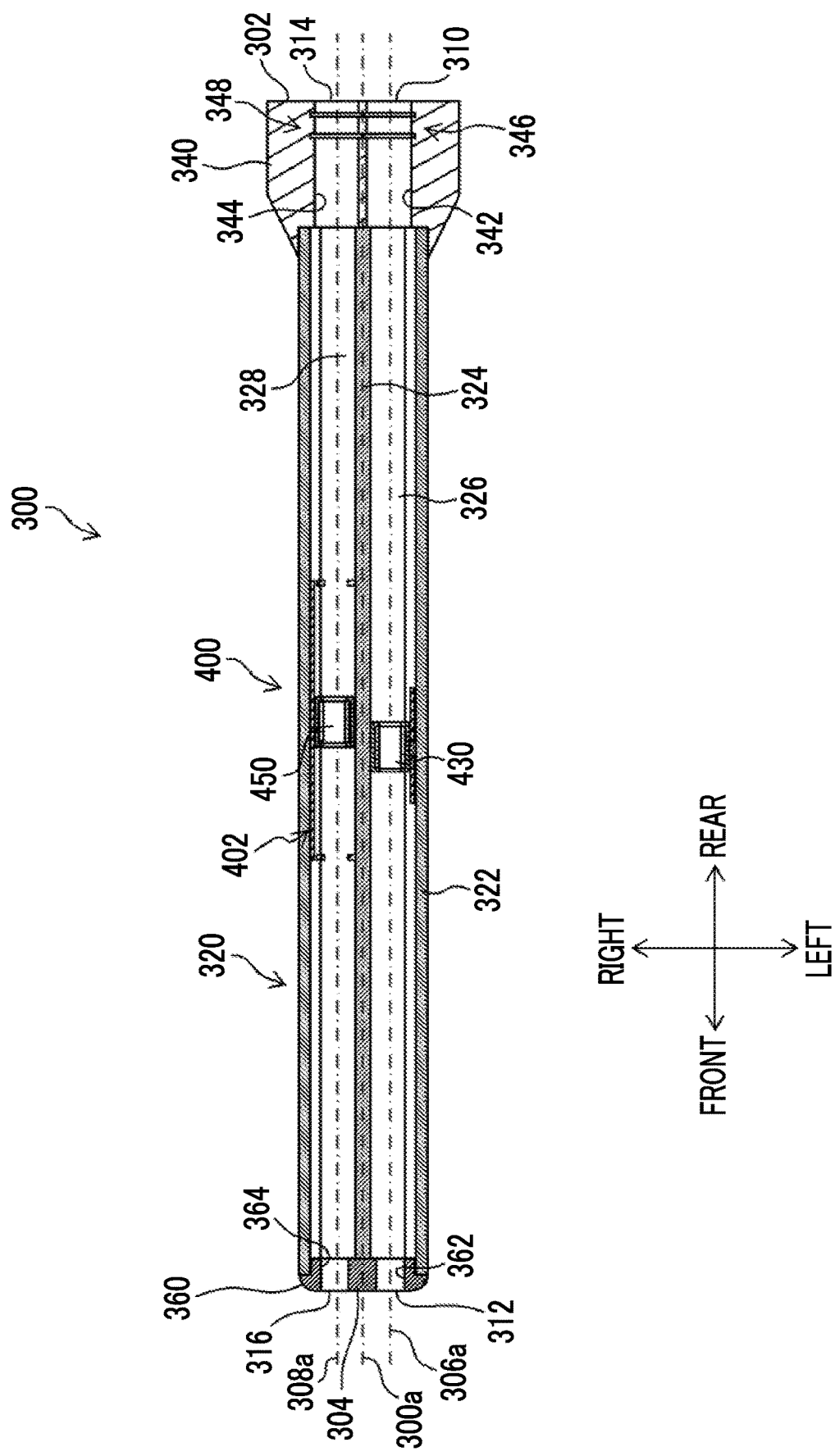
FIG. 12 is a cross sectional view of the overtube cut in a plane (horizontal plane), including the longitudinal axis, which is orthogonal to the upward-downward direction.

FIG. 12 is a cross sectional view of the overtube 300 cut in a plane (horizontal plane), including the longitudinal axis 300a, which is orthogonal to the upward-downward direction. The proximal end cap 340 is provided with a through-hole 342 and a through-hole 344 that form a portion of the endoscope insertion passage 306 and a portion of the treatment tool insertion passage 308, respectively. The through-hole 342 and the through-hole 344 respectively communicate with the endoscope guide groove 326 and the treatment tool guide groove 328 of the long tubular overtube part 320.

Additionally, the through-hole 342 is provided with a valve member 346, and the through-hole 344 is provided with a valve member 348. The valve member 346 and the valve member 348, for example, open only in a case where the endoscope insertion part 102 and the treatment tool insertion part 202 are inserted therethrough and come in close contact with outer peripheral surfaces (side surfaces) of the endoscope insertion part 102 and the treatment tool insertion part 202 without a substantial gap. This secures the airtightness of spaces closer to the distal end side than the valve member 346 and the valve member 348, and reduces the leakage or the like of pneumoperitoneum gas injected into the body cavity to the outside of the body.

The distal end cap 360 is provided with a through-hole 362 and a through-hole 364 that form a portion of the endoscope insertion passage 306 and a portion of the treatment tool insertion passage 308, respectively. The through-hole 362 and the through-hole 364 respectively communicate with the endoscope guide groove 326 and the treatment tool guide groove 328 of the long tubular overtube part 320.

[Configuration of Endoscope]

Figure 13:
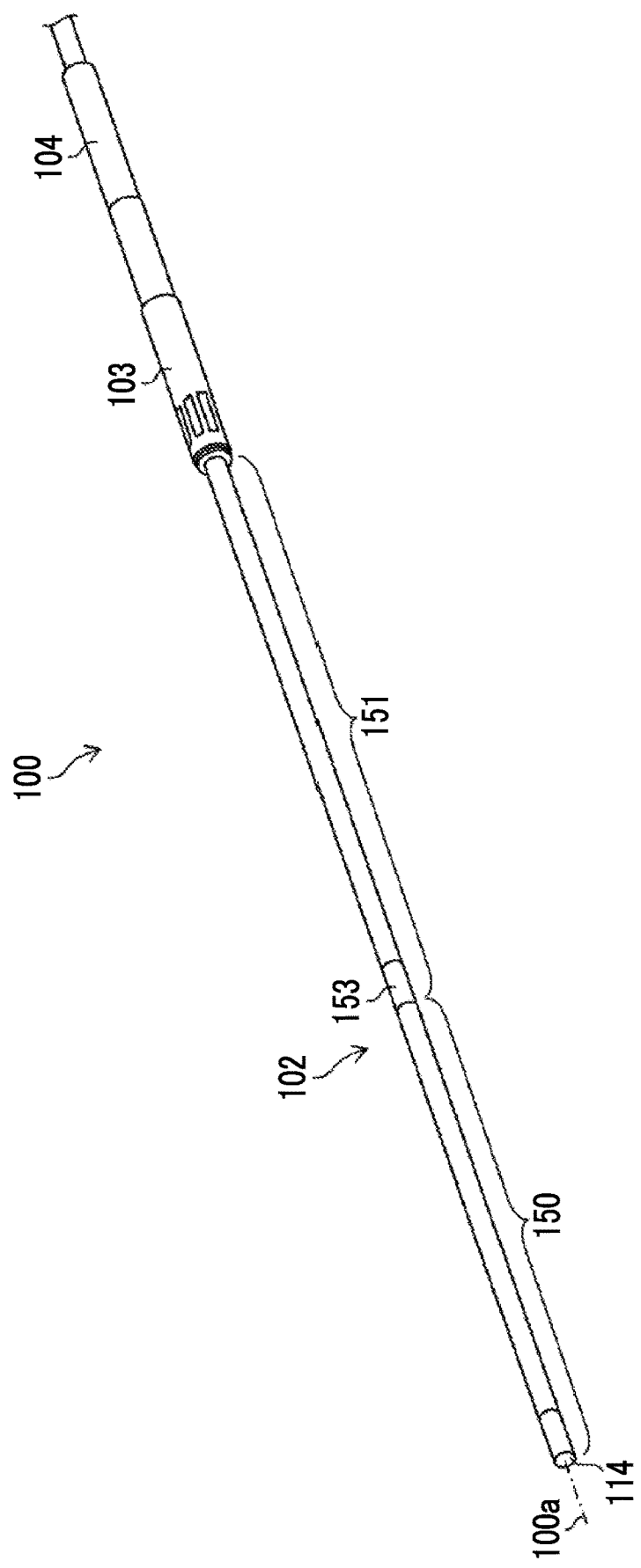
FIG. 13 is an external perspective view of an endoscope insertion part of the endoscope.

FIG. 13 is an external perspective view of the endoscope insertion part 102 of the endoscope 100. As illustrated in FIG. 13, the endoscope insertion part 102 is insertable through the endoscope insertion passage 306, has a distal end, a proximal end, and the endoscope longitudinal axis 100a, and is locked to the slider 400 by the endoscope fixture 430. The endoscope insertion part 102 has a first insertion part 150 that is provided on a distal end side of the endoscope insertion part 102 and the aforementioned distal end surface 114, and a second insertion part 151 that is provided on a proximal end side of the first insertion part 150, is connected to the aforementioned connecting part 103, and has an external diameter larger than that of the first insertion part 150. Additionally, the second insertion part 151 is provided with a held part 153 that is held by the endoscope fixture 430 from a distal end thereof toward a proximal end side thereof.

Figure 14:
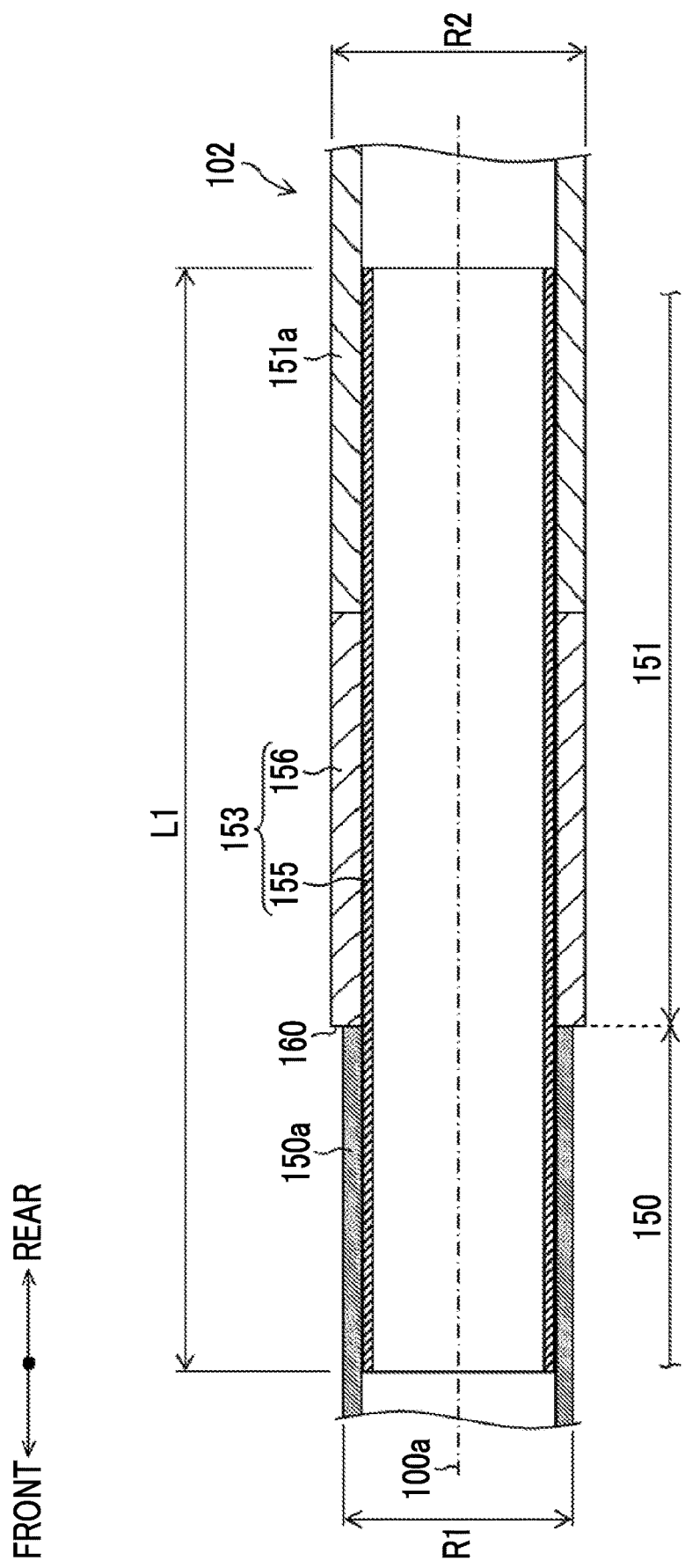
FIG. 14 is a cross sectional view of a held part of the endoscope insertion part along an endoscope longitudinal axis.
Figure 15:
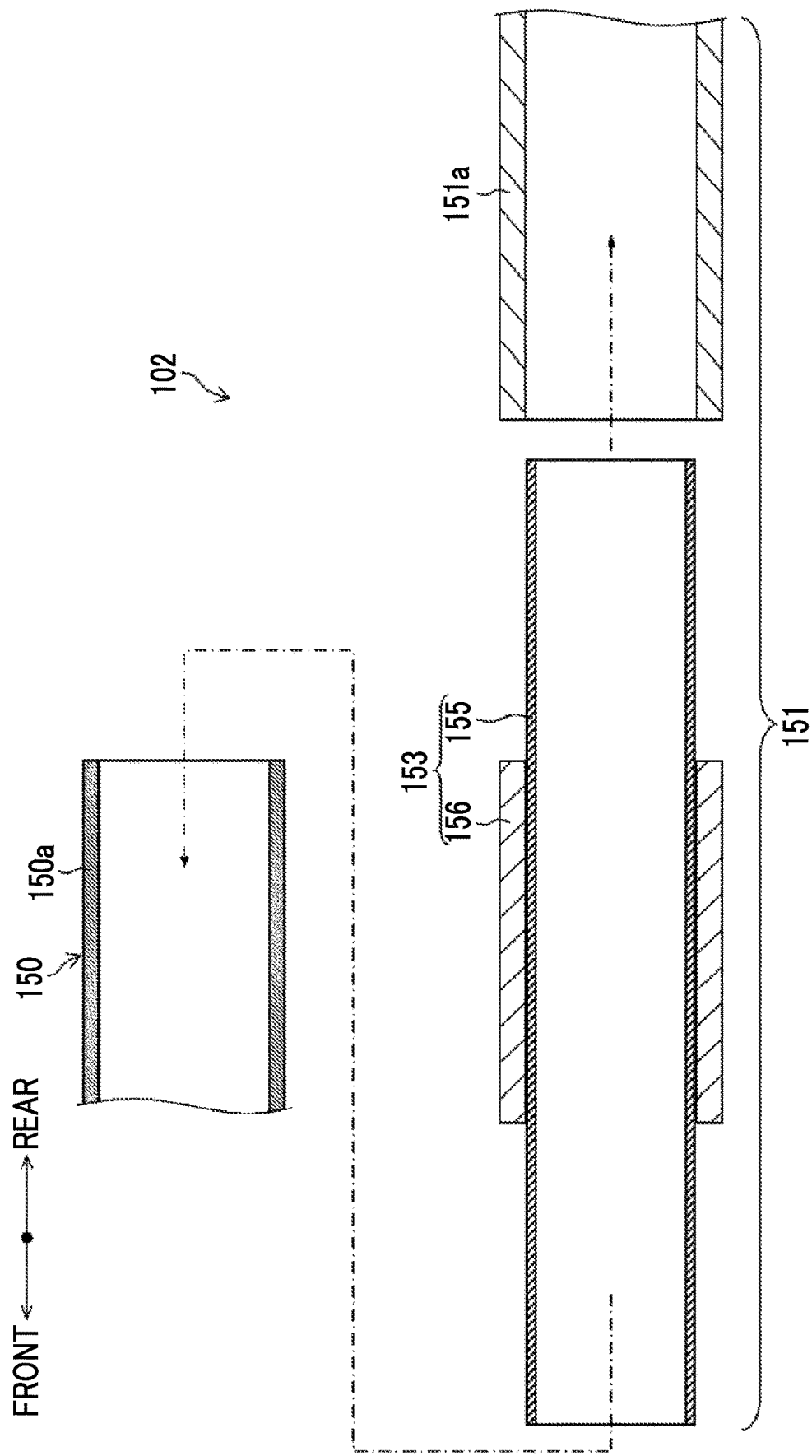
FIG. 15 is an exploded view of the endoscope insertion part.

FIG. 14 is a cross sectional view of the held part 153 of the endoscope insertion part 102 along the endoscope longitudinal axis 100a, and FIG. 15 is an exploded view of the endoscope insertion part 102. In addition, in FIG. 14 and subsequent drawings, in order to prevent complication of the drawings, illustration of signal lines, optical fiber cables, and the like that are inserted through the endoscope insertion part 102 are omitted.

As illustrated in FIGS. 14 and 15, the first insertion part 150 has a metallic tubular body 150a that extends in a direction parallel to the endoscope longitudinal axis 100a. The observation optical system and the solid-state image pick-up element that constitute the aforementioned observation part are provided within the tubular body 150a, the signal lines and the optical fiber cables are inserted through the tubular body 150a. An external diameter R1 of the first insertion part 150 is slightly smaller than the internal diameter of the aforementioned endoscope fixture 430 (the holding frame 432 and the endoscope elastic holder 434), that is, the first insertion part 150 is formed with a size such that the resistance thereof is hardly generated in a case where the first insertion part 150 is inserted through an inner periphery of the endoscope fixture 430.

The second insertion part 151 has a metallic tubular body 151a which extends in the direction parallel to the endoscope longitudinal axis 100a and through which the signal lines and the optical fiber cables are inserted. An external diameter R2 (R2>R1) of the second insertion part 151 (held part 153) is a size designed for the internal diameter of the aforementioned endoscope fixture 430 (the holding frame 432 and the endoscope elastic holder 434), that is, a size such that the resistance thereof is hardly generated in a case where the second insertion part 151 is fitted to the inner periphery of the endoscope fixture 430. For example, the external diameter R1 is 3.7 mm, and the external diameter R2 is 3.8 mm.

The held part 153 has a metallic tubular body 155 which extends in the direction parallel to the endoscope longitudinal axis 100a and through which the signal lines and the optical fiber cables are inserted, and a tubular member 156 that is externally fitted to an outer peripheral surface of a central part of the tubular body 155 and has an insulation property.

A distal end part of the tubular body 155 extend forward of the tubular member 156, and has a shape and an external diameter such that the tubular body 155 is fittable to an inner periphery of the tubular body 150a of the first insertion part 150. Additionally, a proximal end part of the tubular body 155 extends backward of the tubular member 156, and has a shape and an external diameter such that the tubular body 155 is fittable to an inner periphery of the tubular body 151a of the second insertion part 151. For example, a length L1 of the tubular body 155 in the direction of the endoscope longitudinal axis 100a is 40 mm.

As the distal end part of the tubular body 155 is fitted to the inner periphery of the tubular body 150a and the proximal end part of the tubular body 155 is fitted to the inner periphery of the tubular body 151a, the second insertion part 151 is provided so as to be continuous with the first insertion part 150 via the tubular body 155 (held part 153). Additionally, the tubular member 156 (held part 153) is provided from the distal end of the second insertion part 151 toward the proximal end side thereof.

Figure 16:
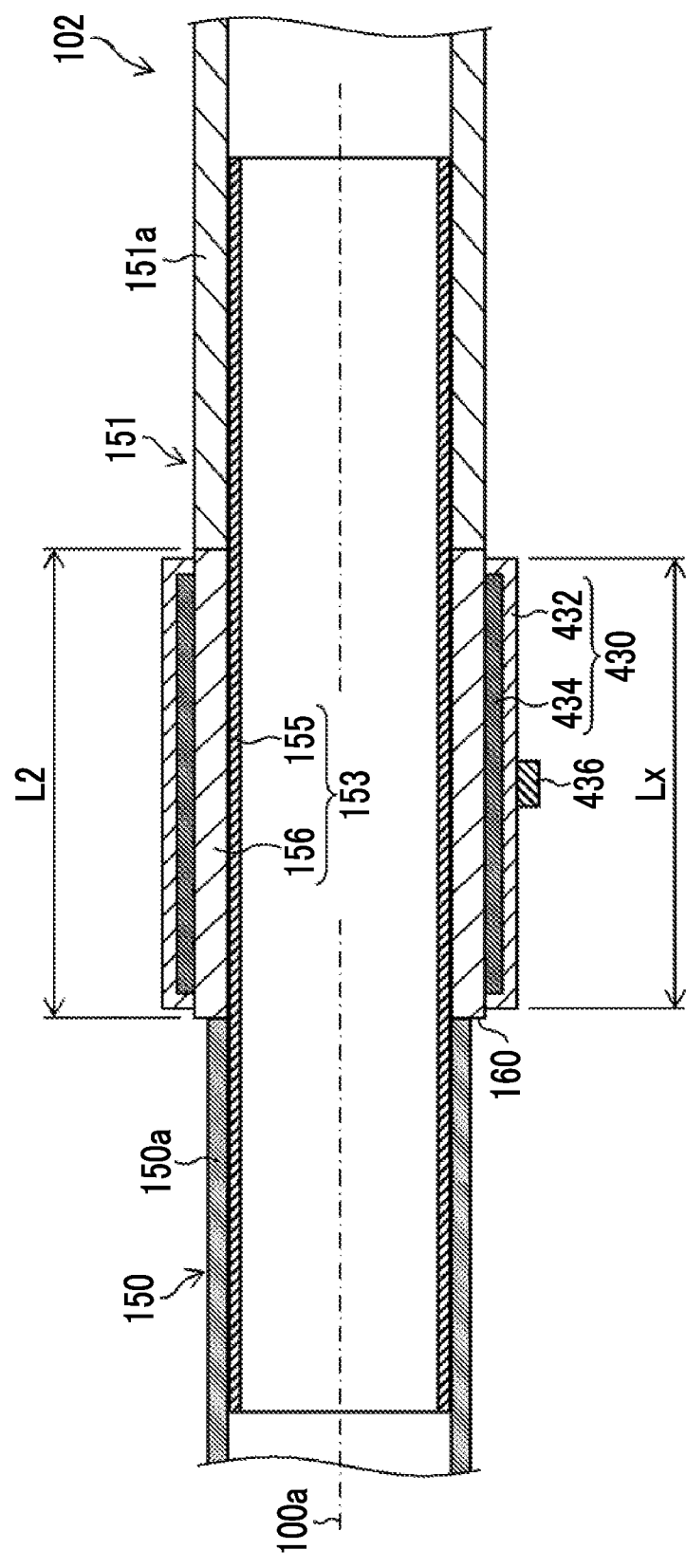
FIG. 16 is a cross sectional view of an endoscope fixture and the held part along the endoscope longitudinal axis.

The tubular member 156 has the external diameter R2, and the outer peripheral surface thereof becomes a held surface held by the endoscope fixture 430 (the holding frame 432 and the endoscope elastic holder 434) (refer to FIG. 16). The tubular member 156 is formed of an insulating member of the invention, such as resin or ceramics, having an insulation property. In addition, only a surface that comes into contact with at least the inner periphery of the endoscope fixture 430 may be formed of the insulating member instead of forming the entire tubular member 156 of the insulating member. Additionally, since the external diameter R2 of the tubular member 156 is larger than the external diameter R1 of the first insertion part 150, a stepped part 160 is formed on the outer peripheral surface of the endoscope insertion part 102 at a boundary between the first insertion part 150 and the held part 153 (second insertion part 151).

FIG. 16 is a cross sectional view of the endoscope fixture 430 and the held part 153 along the endoscope longitudinal axis 100a. As illustrated in FIG. 16, in a case where the length of the endoscope fixture 430 in the direction of endoscope longitudinal axis 100a is defined as Lx, the tubular member 156 is formed so as to have at least a length L2 equal to or more than the length Lx from the stepped part 160 to the proximal end side. The length L2 is 12 mm. Accordingly, the metallic holding frame 432 of the endoscope fixture 430 is prevented from coming into contact with points other than the tubular member 156 of the endoscope insertion part 102.

In addition, a restricting member that abuts against a proximal end surface (rear end surface) of the holding frame 432 may be provided at a proximal end part behind an outer peripheral surface of the tubular member 156, and deviation of the endoscope fixture 430 further to the proximal end side than the tubular member 156 is restricted by the restricting member. Accordingly, the metallic holding frame 432 is reliably prevented from coming into contact with points other than the tubular member 156 of the endoscope insertion part 102.

[Operation of Surgery System]

Next, the operation of the surgery system 10 of the above configuration will be described. FIGS. 17A and 17B are illustrative views for illustrating the holding of the endoscope insertion part 102 by the endoscope fixture 430 of the overtube 300. The operator inserts the endoscope insertion part 102 into the endoscope insertion passage 306 from the first proximal end opening 310 (refer to FIG. 2) of the proximal end cap 340 after inserting the overtube 300 into the patient's body wall together with the outer sheath 500. The distal end of the first insertion part 150 of the endoscope insertion part 102 protrudes into the patient's body cavity from the first distal end opening 312 after advancing along the endoscope insertion passage 306 (endoscope guide groove 326) and being inserted through the inner periphery of the annular endoscope fixture 430 (the holding frame 432 and the endoscope elastic holder 434).

In this case, as illustrated in FIG. 17A, since the external diameter R1 (refer to FIG. 14) of the first insertion part 150 is slightly smaller than the internal diameter of the endoscope fixture 430, resistance is hardly generated even in a case where the first insertion part 150 is inserted through the inner periphery of the endoscope fixture 430. Then, in a case where the operator continues the insertion operation of the endoscope insertion part 102 into the endoscope insertion passage 306, as illustrated in FIG. 17B, the stepped part 160 formed by the held part 153 (tubular member 156) of the second insertion part 151 reaches an opening of the inner periphery of the endoscope fixture 430. Since the external diameter R2 (refer to FIG. 14) of the held part 153 is larger than the aforementioned external diameter R1, a resistance force that resists the insertion operation is generated in a case where the stepped part 160 reaches the opening of the inner periphery of the endoscope fixture 430. For this reason, the operator can discriminate that the stepped part 160 has reached the endoscope fixture 430 within the endoscope insertion passage 306 simply with the feeling of his/her hand that performs the insertion operation.

Next, in a case where the operator continues the insertion operation against the resistance force, the tubular member 156 of the held part 153 is fitted to the inner periphery of the endoscope fixture 430, and the held part 153 is held by the endoscope fixture 430 (refer to FIG. 16). By making the external diameter R2 of the second insertion part 151 (held part 153) larger than the external diameter R1 of the first insertion part 150 in this way, the operator can simply hold the held part 153 of the endoscope insertion part 102 with the endoscope fixture 430 with his/her hand's feeling even in a case where the inside of the overtube 300 cannot be seen.

Figure 18:
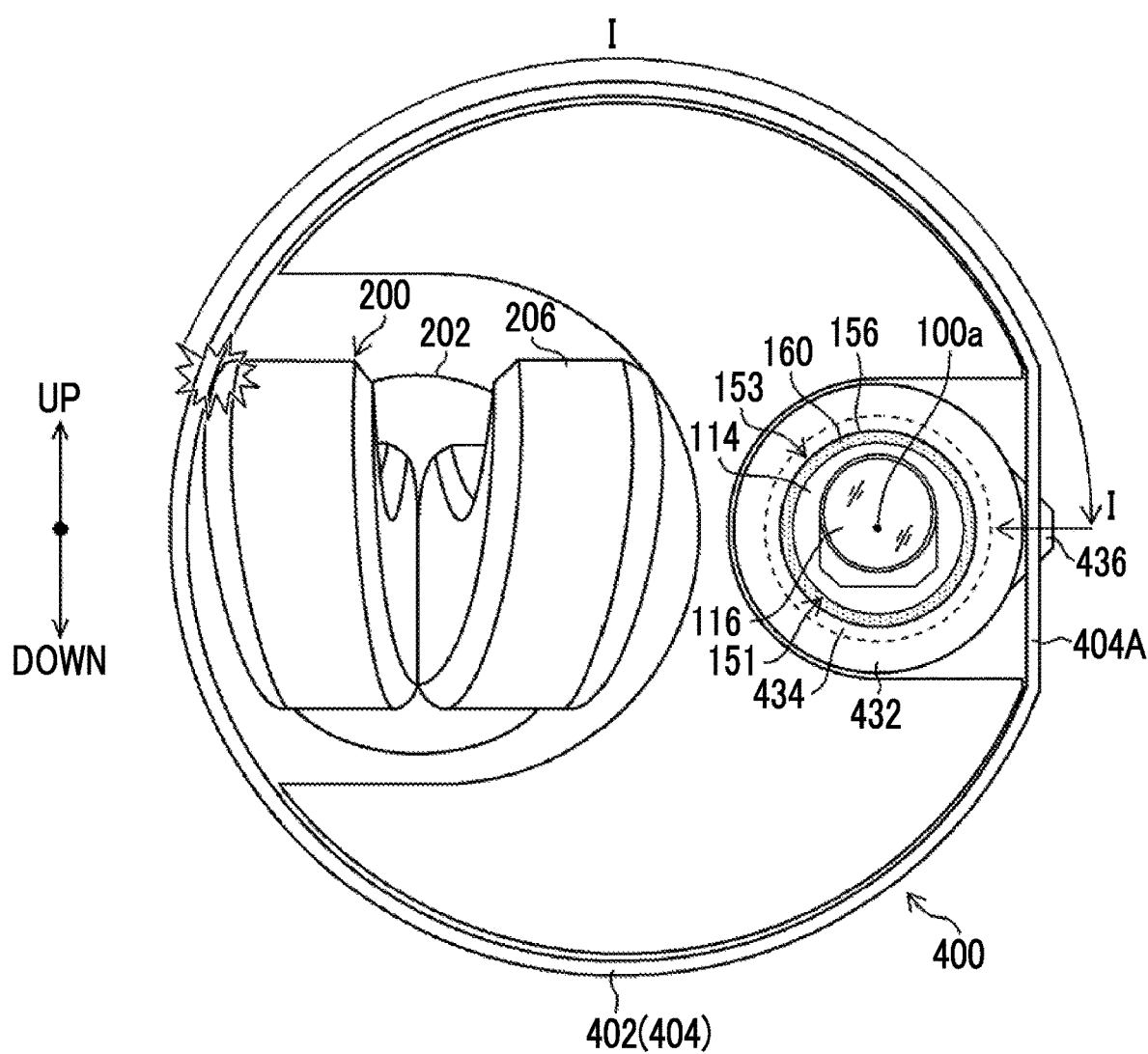
FIG. 18 is a cross sectional view taken along line "18-18" in FIG. 6.
Figure 19:
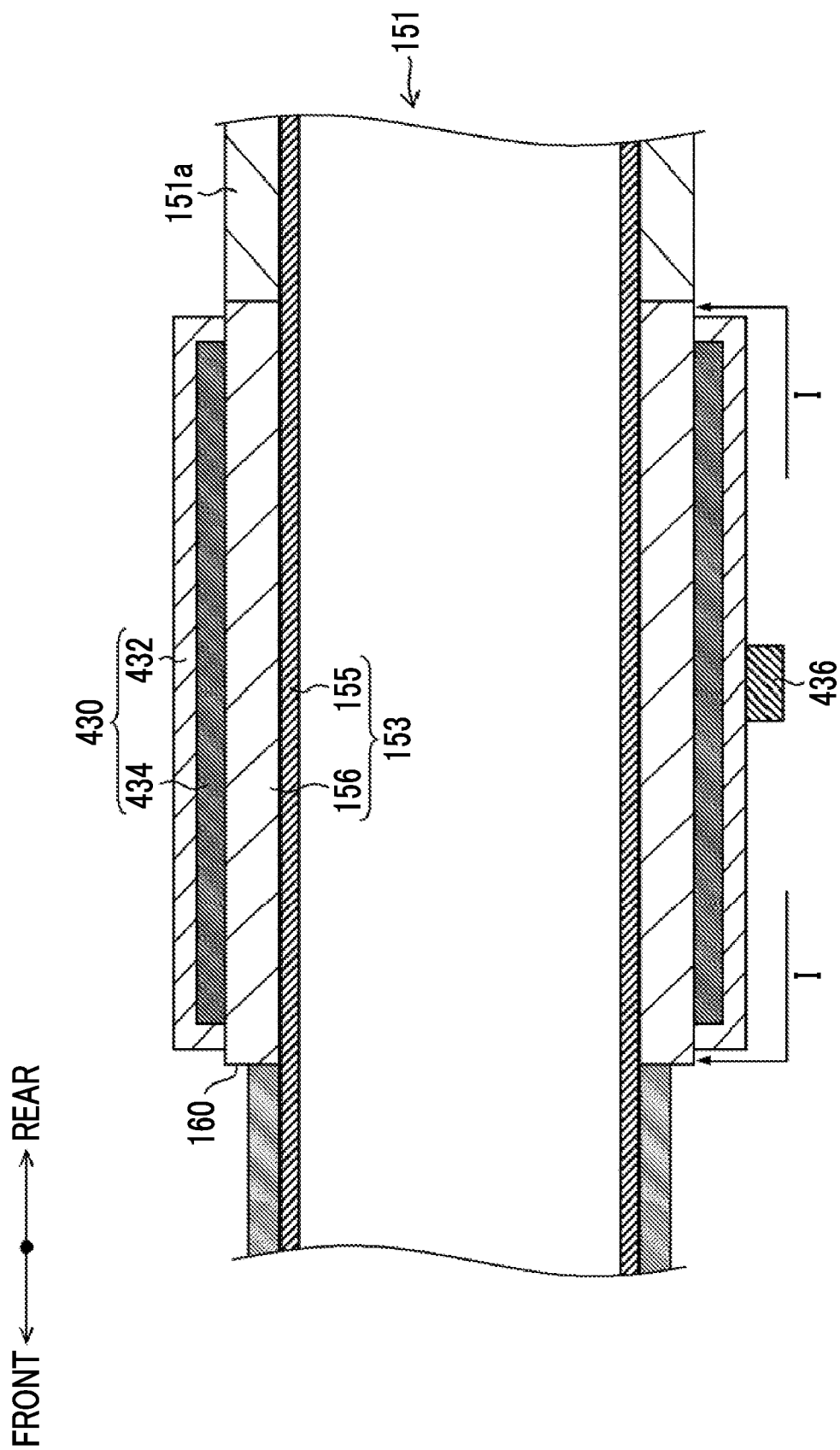
FIG. 19 is a cross sectional view of the held part and the endoscope fixture cut in the horizontal plane, including the endoscope longitudinal axis, which is orthogonal to the upward-downward direction.

FIG. 18 is a cross sectional view taken along line "18-18" in FIG. 6. FIG. 19 is a cross sectional view of the held part 153 and the endoscope fixture 430 cut in the horizontal plane, including the endoscope longitudinal axis 100a, which is orthogonal to the upward-downward direction. As illustrated in FIGS. 18 and 19, in a case where the treatment tool 200 is inserted along the treatment tool insertion passage 308 (treatment tool guide groove 328) from the second proximal end opening 314 or in a case where the treatment tool 200 is detached from the treatment tool insertion passage 308, there is a concern that the treatment part 206 that generates a high-frequency current I may come into contact with the coupling ring 402 (ring part 404) of the slider 400.

In such a case, in a case where the operator erroneously applies an electric current to the treatment tool 200, the high-frequency current I generated from the treatment part 206 flows up to the holding frame 432 through the coupling ring 402 (ring part 404), the first engaging part 404A, and the protrusion 436. In this case, since the tubular member 156 of the held part 153 of the endoscope 100 in contact with a portion of the inner peripheral surface of the holding frame 432 has an insulation property, the high-frequency current I is prevented from leaking from the holding frame 432 through the held part 153 to the endoscope 100 side.

[Effects of Present Embodiment]

In the present embodiment as described above, at least the surface of the held part 153 of the endoscope 100 held by the endoscope fixture 430 within the endoscope insertion passage 306 of the overtube 300 is formed of at least the insulating member. Thus, the insulation between the endoscope 100 and the treatment tool 200 is ensured even in a case where the slider 400 is formed of metals. As a result, for example, even in a case where the high-frequency current I generated from the treatment part 206 of the treatment tool 200 flows up to the holding frame 432 of the endoscope fixture 430 through the slider 400, the high-frequency current I is prevented from leaking to the endoscope 100 side. Accordingly, electronic components, such as the solid-state image pick-up element built in the observation part of the endoscope 100, are prevented from being damaged due to the high-frequency current I.

Additionally, since the external diameter of the second insertion part 151 is made larger than the external diameter of the first insertion part 150 and the aforementioned held part 153 is provided from the distal end of the second insertion part 151 toward the proximal end side thereof, the operator can simply hold the held part 153 of the endoscope insertion part 102 with the endoscope fixture 430 simply with his/her hand's feeling even in a case where the inside of the overtube 300 cannot be seen.

Moreover, since the slider 400 can be formed of metals and thinned, the overtube 300 can be thinly formed.

[Endoscope of Further Embodiment 1]

Figure 20:
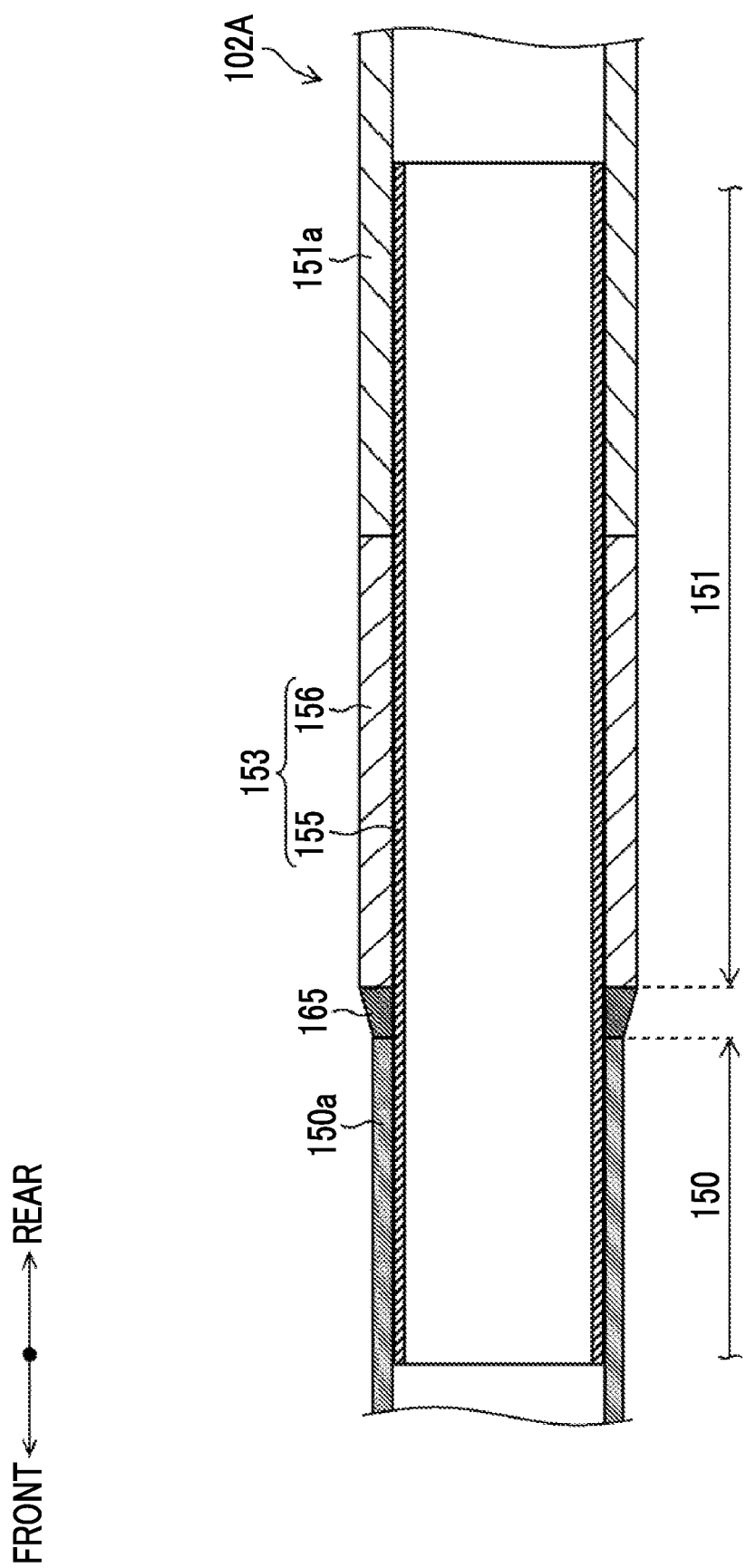
FIG. 20 is a cross sectional view of an endoscope insertion part of the endoscope in a further Embodiment 1.

FIG. 20 is a cross sectional view of an endoscope insertion part 102A of the endoscope 100 of a further Embodiment 1. In the endoscope insertion part 102 of the endoscope 100 of the above embodiment, the second insertion part 151 (held part 153) is provided so as to be continuous with a proximal end part of the first insertion part 150. For example, as illustrated in FIG. 20, an annular tapered part 165 may be provided between the first insertion part 150 and the second insertion part 151 as in the endoscope insertion part 102A.

The tapered part 165 is externally fitted to an outer peripheral surface of the tubular body 155 at a position between the first insertion part 150 and the second insertion part 151 (tubular member 156). The tapered part 165 is formed such that the external diameter thereof becomes gradually larger from the first insertion part 150 toward the second insertion part 151. Accordingly, the inclination of the stepped part 160 on the outer peripheral surface of the endoscope insertion part 102 as described in the above embodiment becomes gentle. As a result, in a case where the operator performs the insertion operation of the endoscope insertion part 102 into the endoscope insertion passage 306, the held part 153 can be reliably guided to the inner periphery of the endoscope fixture 430 without the stepped part 160 of the held part 153 being caught in an opening edge of the inner periphery of the endoscope fixture 430. Accordingly, the held part 153 can be reliably held by the endoscope fixture 430.

[Endoscope of Further Embodiment 2]

FIG. 21A is a cross sectional view of an endoscope insertion part 102B of the endoscope 100 of a further Embodiment 2. In the endoscope insertion part 102 of the endoscope 100 of the above embodiment, the two insertion parts, first insertion part 150 and second insertion part 151, having different external diameters are formed so as to be continuous with each other. However, the endoscope insertion part 102B of the further Embodiment 2 is formed based on one tubular body 169.

As illustrated in FIG. 21A, an outer peripheral surface of a distal end part on a front side of the tubular body 169 is thinned by grinding processing or polishing processing, and an insulating held part 170 held by the endoscope fixture 430 so as to cover an outer peripheral surface of a proximal end part on a rear side of the tubular body 169 is provided in a thinned region of the tubular body 169. Specifically, a tubular member having at least an insulating surface may be externally fitted, as the held part 170, to the proximal end part of the thinned region of the tubular body 169, or an insulating material may be applied and cured on the proximal end part to form the held part 170.

The external diameter of the held part 170 is the same (including substantially the same) as the external diameter of a non-thinned region of the tubular body 169. Accordingly, a stepped part 171 resulting from the distal end of the held part 170 is formed on an outer peripheral surface of the endoscope insertion part 102B.

With the stepped part 171 as a border, the endoscope insertion part 102B has a first insertion part 172 on the front side with respect to the stepped part 171 and a second insertion part 173 on the rear side (proximal end side) with respect to the stepped part 171 and having an external diameter larger than that of the first insertion part 172. Additionally, the endoscope insertion part 102B has the insulating held part 170 provided from a distal end of the second insertion part 173 toward a proximal end side thereof. Therefore, since the endoscope insertion part 102B basically has the same configuration as the endoscope insertion part 102 of the above embodiment, the same effects as the above embodiment are obtained in a case where the endoscope insertion part 102B is inserted through the overtube 300.

FIG. 21B is a cross sectional view of the endoscope insertion part 102B of the endoscope 100 provided with a tapered part 175 in the still further Embodiment 2. As illustrated in FIG. 21B, also in the endoscope insertion part 102B of the still further Embodiment 2, similar to the endoscope insertion part 102A (refer to FIG. 20) of the above further Embodiment 1, the tapered part 175 of which the external diameter becomes gradually larger from the first insertion part 172 toward the second insertion part 173 may be provided between the first insertion part 172 and the second insertion part 173.

[Endoscope of Still Further Embodiments 3 and 4]

Figure 22A:
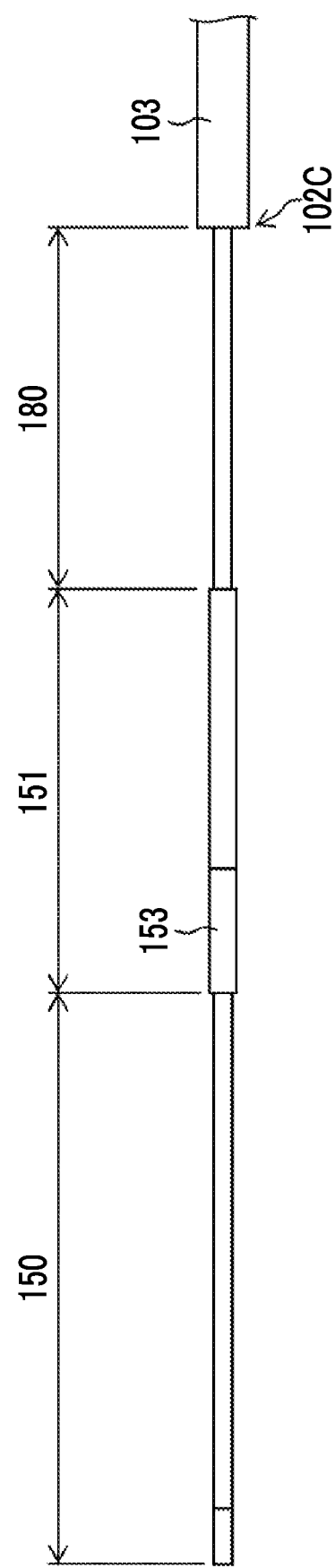
FIG. 22A is a side view of an endoscope insertion part of an endoscope in a still further Embodiment 3.
Figure 22B:
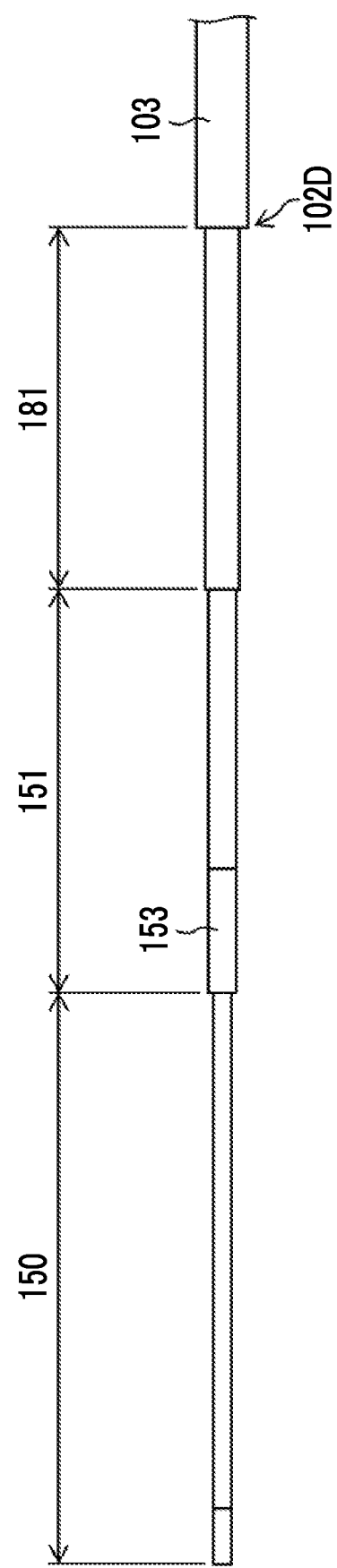
FIG. 22B is a side view of an endoscope insertion part of an endoscope in a still further Embodiment 4.

FIG. 22A is a side view of an endoscope insertion part 102C of the endoscope 100 of a still further Embodiment 3. FIG. 22B is a side view of an endoscope insertion part 102D of the endoscope 100 of a still further Embodiment 4. Although the endoscope insertion part 102 of the endoscope 100 of the above embodiment has an external diameter that is more uniform on the proximal end side than at the stepped part 160, a separate insertion part having an external diameter different from the second insertion part 151 may be provided between the second insertion part 151 and the connecting part 103 as in the still further Embodiments 3 and 4.

As illustrated in FIG. 22A, the endoscope insertion part 102C of the still further embodiment 3 has a third insertion part 180, having an external diameter smaller than that of the second insertion part 151, on a proximal end side of the second insertion part 151. The third insertion part 180 is inserted through the valve member 346 within the through-hole 342 illustrated in FIG. 12 as already described at the time of use of the surgery system 10. For this reason, the valve member 346 comes into close contact with an outer peripheral surface of the third insertion part 180. In this case, since the external diameter of the third insertion part 180 is made smaller than the external diameter of the second insertion part 151, the sliding resistance of the third insertion part 180 and the valve member 346 can be reduced as compared with the above embodiment in a case where the endoscope insertion part 102C is moved forward and backward in the forward-backward direction or is rotated around the endoscope longitudinal axis 100a.

Meanwhile, as illustrated in FIG. 22B, the endoscope insertion part 102D of the still further embodiment 4 has a fourth insertion part 181, having an external diameter larger than that of the second insertion part 151, on the proximal end side of the second insertion part 151. By providing this fourth insertion part 181, the rigidity of the endoscope insertion part 102D can be made higher than that of the endoscope insertion part 102 of the above embodiment. Thus, the endoscope insertion part 102D is prevented from deflecting at the time of use of the surgery system 10. As a result, since a situation where, due to the deflection of the endoscope insertion part 102D, the range of an observation site reflected on the endoscopic image 119 varies or blur occurs in the endoscopic image 119 is prevented. Therefore, an image that is desired by an operator is obtained.

[Other Modification Examples of Endoscope]

Although the external diameter of the second insertion part 151 including the held part 153 is uniformly formed in the above embodiments, the external diameters of the held part 153 and the tubular body 151a that constitutes the second insertion part 151 may be made different from each other (refer to FIG. 16). For example, by making the external diameter of the tubular body 151a smaller than the external diameter of the held part 153, the contact between the endoscope insertion parts 102 and the endoscope fixture 430 (holding frame 432) excluding the held part 153 can be prevented regardless of the holding position of the held part 153 by the endoscope fixture 430. As a result, the high-frequency current I can be more reliably from leaking from the holding frame 432 toward the endoscope 100 side.

[Others]

In the above individual embodiments, the rigid endoscope has been described as an example as the endoscope of the invention. However, the invention can be applied to various kinds of endoscopes to be insertable through the overtube 300 and used in combination with the overtube 300.

In the above individual embodiments, the overtube 300 is inserted through the outer sheath 500. However, the invention can also be applied to a case where the overtube 300 directly punctures a body wall without being inserted through the outer sheath 500.

Explanation of References

10: surgery system
100: endoscope

100a: endoscope longitudinal axis
102: endoscope insertion part
102A: endoscope insertion part
102B: endoscope insertion part
102C: endoscope insertion part
102D: endoscope insertion part
103: connecting part
104: cord part
108: processor device
110: light source device
112: monitor
114: distal end surface
116: observation window
119: endoscopic image
150: first insertion part
150a: tubular body
151: second insertion part
151a: tubular body
153: held part
155: tubular body
156: tubular member
160: stepped part
165: tapered part
169: tubular body
170: held part
171: stepped part
172: first insertion part
173: second insertion part
175: tapered part
180: third insertion part
181: fourth insertion part
200: treatment tool
202: treatment tool insertion part
204: operating part
206: treatment part
300: overtube
300a: longitudinal axis
302: proximal end surface
304: distal end surface
306a: endoscope insertion axis
306: endoscope insertion passage
308: treatment tool insertion passage
308a: treatment tool insertion axis
310: first proximal end opening
312: first distal end opening
314: second proximal end opening
316: second distal end opening
320: long tubular overtube part
322: long tubular body
324: partition wall member
324A: partition wall member
326: endoscope guide groove
328: treatment tool guide groove
340: proximal end cap
342: through-hole
344: through-hole
346: valve member
348: valve member
360: distal end cap
362: through-hole
364: through-hole
400: slider
402: coupling ring
404: ring part
404A: first engaging part
406: arm part
408: rear restriction end
408A: opening
410: front restriction end
410A: opening
412: engaging hole
420: endoscope coupling part
422: treatment tool coupling part
430: endoscope fixture
432: holding frame
434: endoscope elastic holder
434a: endoscope holding surface
436: protrusion
450: treatment tool fixture
452: frame
454: treatment tool elastic holder
454a: treatment tool holding surface
500: outer sheath
500a: distal end opening
500b: proximal end opening
504: longitudinal groove
520: lateral groove
I: high-frequency current

What is claimed is:

1. A surgery system comprising:
an overtube that has a distal end, a proximal end, and a longitudinal axis and holds a treatment tool and an endoscope so as to be movable forward and backward in a direction of the longitudinal axis, the overtube having
a metallic movable body that is provided within the overtube and is movable in the longitudinal axis direction inside the overtube,
an endoscope holding part that is provided within the movable body and holds the endoscope, wherein the endoscope holding part has an endoscope holding surface, and
a treatment tool holding part that is provided within the movable body and holds the treatment tool, wherein the treatment tool holding part has a treatment tool holding surface;
the endoscope that has an insertion part which is insertable into the overtube and has a distal end, a proximal end, and a longitudinal axis and that is locked to the movable body by the endoscope holding part,
wherein the insertion part comprises
a first insertion part that is provided on a distal end side of the insertion part,
a second insertion part that is provided on a proximal end side of the first insertion part and has an external diameter larger than that of the first insertion part, and
a held part that is provided on a distal end of the second insertion part, the held part comprises:
a metallic tubular body extending along the longitudinal axis of the insertion part; and
a tubular member disposed on an outer peripheral surface of a central part of the metallic tubular body only, and is held by the endoscope holding part, and has an insulation property; and
the treatment tool that is inserted into the overtube and locked to the movable body by the treatment tool holding part.

2. The surgery system according to claim 1,
wherein the endoscope holding part has a metallic holding frame, and an annular elastic holder that is provided within the holding frame and elastically holds the held part.

3. The surgery system according to claim 1,
wherein the second insertion part is provided so as to be continuous with the first insertion part.

4. The surgery system according to claim 1,
wherein a tapered part of which an external diameter becomes gradually larger from the first insertion part toward the second insertion part is provided between the first insertion part and the second insertion part.

5. The surgery system according to claim 1,
wherein the insertion part has a third insertion part that is provided on the proximal end side of the second insertion part and has an external diameter smaller than that of the second insertion part.

6. The surgery system according to claim 1,
wherein the insertion part has a fourth insertion part that is provided on the proximal end side of the second insertion part and has an external diameter larger than that of the second insertion part.

7. The surgery system according to claim 1,
wherein the overtube has an endoscope insertion passage through which the endoscope is inserted so as to be movable forward and backward, a treatment tool insertion passage through which the treatment tool is inserted so as to be movable forward and backward, and a partition wall member having a partition wall between the endoscope insertion passage and the treatment tool insertion passage, and
wherein the movable body has a ring body that is externally fitted to an outer peripheral part of the partition wall member, the endoscope holding part and the treatment tool holding part is provided inside the ring body, and the movable body has an endoscope locking part to which the endoscope holding part is locked, and a treatment tool locking part to which the treatment tool holding part is locked, and has a region where either the endoscope or the treatment tool is moved forward and backward in an interlocking manner with the forward and backward movement of the other.

8. The surgery system according to claim 7,
wherein the endoscope holding part has a holding frame, and an annular elastic holder that is provided within the holding frame and elastically holds the held part, and is movable forward and backward along the endoscope insertion passage,
wherein the treatment tool holding part moves so as to be movable forward and backward along the treatment tool insertion passage,
wherein the endoscope locking part has a first restricting part that is provided at the ring body and restricts the forward and backward movement of the endoscope holding part with respect to the ring body in a first range, the first restricting part being engaged with the holding frame,
wherein the treatment tool locking part has a second restricting part that is provided at the ring body, restricts the forward and backward movement of the treatment tool holding part with respect to the ring body in a second range different from the first range, and
wherein at least the holding frame, the ring body, and the first restricting part are made of metal.

9. The surgery system according to claim 7,
wherein the movable body has a region where either the endoscope or the treatment tool is not moved forward and backward in an interlocking manner with the forward and backward movement of the other.

10. An endoscope, configured to be used with an overtube that has a distal end, a proximal end, and a longitudinal axis and holds a treatment tool and the endoscope so as to be movable forward and backward in a direction of the longitudinal axis,
wherein the overtube comprises
a metallic movable body that is provided within the overtube and is movable in the longitudinal axis direction inside the overtube,
an endoscope holding part that is provided within the movable body and holds the endoscope, wherein the endoscope holding part has an endoscope holding surface, and
a treatment tool holding part that is provided within the movable body and holds the treatment tool, wherein the treatment tool holding part has a treatment tool holding surface,
the endoscope comprising:
an insertion part which is insertable into the overtube and has a distal end, a proximal end, and a longitudinal axis and that is locked to the movable body by the endoscope holding part,
wherein the insertion part comprises
a first insertion part that is provided on a distal end side of the insertion part;
a second insertion part that is provided on a proximal end side of the first insertion part and has an external diameter larger than that of the first insertion part; and
a held part that is provided on a distal end of the second insertion part, the held part comprises:
a metallic tubular body extending along the longitudinal axis of the insertion part; and
a tubular member disposed on an outer peripheral surface of a central part of the metallic tubular body only, and is held by the endoscope holding part, and has an insulation property.

* * * * *